US006989098B2

(12) United States Patent
Collins et al.

(10) Patent No.: US 6,989,098 B2
(45) Date of Patent: Jan. 24, 2006

(54) METHODS FOR THE ISOLATION, RECOVERY AND PURIFICATION OF NON-POLAR COMPOUNDS USING NOVEL HYDROPHOBICALLY-MODIFIED POLYSACCHARIDE GELS

(75) Inventors: F. William Collins, Ottawa (CA); A. Bachir Sarr, Ottawa (CA); David Fielder, Edmondton (CA)

(73) Assignee: Her Majesty the Queen in right of Canada, as represented by the Minister of Agriculture and Agri-Food Canada, Ottawa (CA)

( * ) Notice: Subject to any disclaimer, the term of this patent is extended or adjusted under 35 U.S.C. 154(b) by 197 days.

(21) Appl. No.: 10/340,026

(22) Filed: Jan. 10, 2003

(65) Prior Publication Data

US 2003/0150805 A1 Aug. 14, 2003

Related U.S. Application Data

(62) Division of application No. 09/613,110, filed on Jul. 10, 2000, now Pat. No. 6,582,594, which is a continuation of application No. PCT/CA99/00004, filed on Jan. 11, 1999.
(60) Provisional application No. 60/071,251, filed on Jan. 12, 1998.

(51) Int. Cl.
*B01D 15/08* (2006.01)

(52) U.S. Cl. .................... 210/635; 210/656; 210/198.2; 210/502.1
(58) Field of Classification Search ................ 210/635, 210/656, 198.2, 502.1; 525/54.21; 502/402, 502/404; 530/413
See application file for complete search history.

(56) References Cited

U.S. PATENT DOCUMENTS

| 5,470,463 | A | * | 11/1995 | Girot et al. | ............... 210/198.2 |
| 5,482,914 | A | | 1/1996 | Merle | ........................ 502/404 |
| 5,563,241 | A | * | 10/1996 | Beezhold | .................... 528/482 |
| 5,641,539 | A | | 6/1997 | Afeyan et al. | .............. 427/222 |
| 5,759,404 | A | * | 6/1998 | Ericsson et al. | ............ 210/638 |
| 5,906,734 | A | * | 5/1999 | Girot et al. | ............... 210/198.2 |
| 6,080,571 | A | * | 6/2000 | Prior et al. | ................. 435/239 |
| 6,709,743 | B1 | * | 3/2004 | Draveling | ................... 428/402 |

FOREIGN PATENT DOCUMENTS

| EP | 0180563 | 5/1986 |
| EP | 0357479 | 3/1990 |
| GB | 2194900 | 3/1988 |
| WO | WO84/03053 | 8/1984 |

* cited by examiner

*Primary Examiner*—Ernest G. Therkorn
(74) *Attorney, Agent, or Firm*—Reslin Rothenberg Farley & Mesiti P.C.

(57) ABSTRACT

A process is described for the preparation f electrostatically-linked, aliphatic- or alicyclic-substituted anionic or cationic polysaccharide gels from readily available macroporous ionic polysaccharide chromatographic media, such as diethylaminoethyl (DEAE), quaternary aminoethyl (QAE) and sulfopropyl (SP) substituted polysaccharide gels. These novel gels are used for the isolation, recovery and purification of non-polar extractives using one or more extracting solvents from the group of lower alcohols, ketones, and water. The non-polar extractives may be alk(n)lyresorcinols, steroid, triterpenoid, cardiac glycosides and saponins, steryl ferulates and other phenolic acid conjugates, flavonoids, lipids, alcohol-soluble antimicrobials, prolamines or other alcohol-soluble proteolipid complexes.

27 Claims, 12 Drawing Sheets

Avenacin A-1

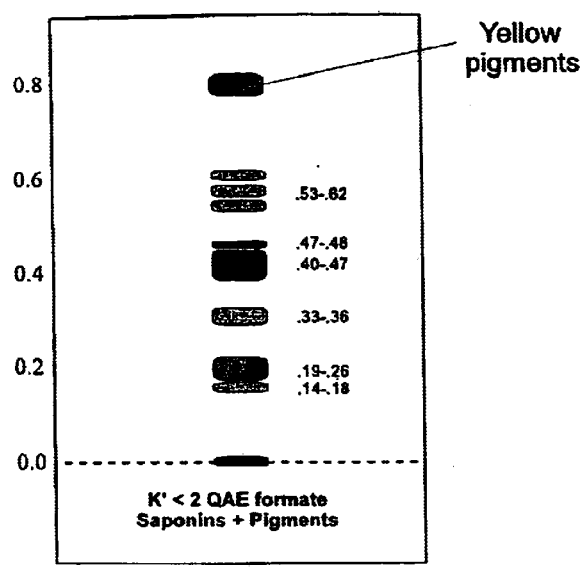
FIG. 7A
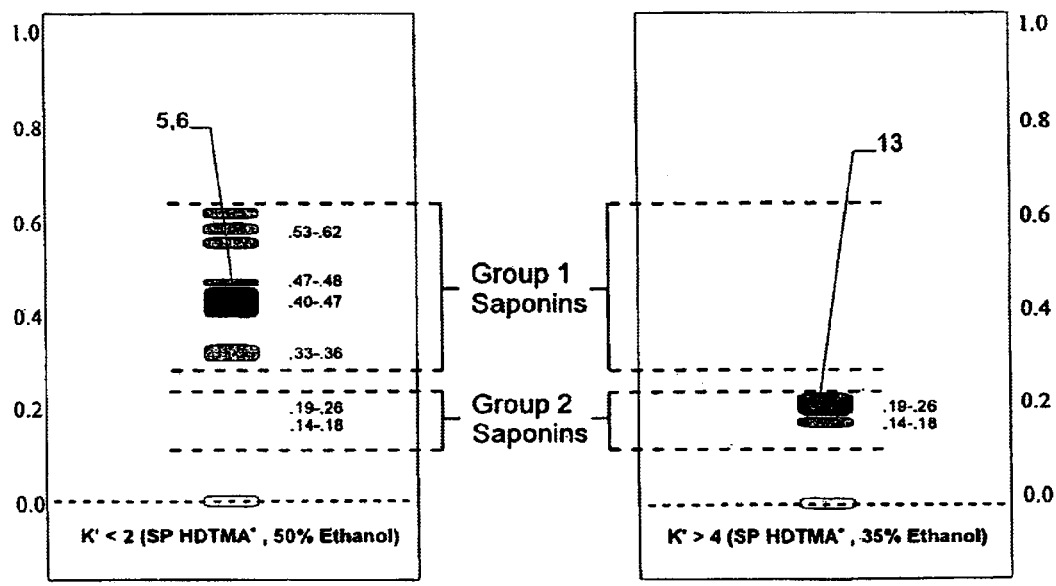
FIG. 7B
FIG. 7C

METHODS FOR THE ISOLATION, RECOVERY AND PURIFICATION OF NON-POLAR COMPOUNDS USING NOVEL HYDROPHOBICALLY-MODIFIED POLYSACCHARIDE GELS

This application is a divisional of U.S. application Ser. No. 09/613,110 now U.S. Pat. No. 6,582,594 filed on Jul. 10, 2000. U.S. application Ser. No. 09/613,110 is a continuation of copending PCT application CA99/00004, filed Jan. 11, 1999, which designated the United States and claimed the priority of U.S. application Ser. No. 60/071,251 filed Jan. 12, 1998. The priorities of all are claimed herein, and the entire disclosures of all are incorporated herein by reference.

The present invention relates to a process for the preparation of electrostatically-linked, aliphatic- or alicyclic-substituted anionic or cationic polysaccharide gels from readily available macroporous ionic polysaccharide chromatographic media. The present invention further relates to the isolation, recovery and purification of non-polar extractives using said polysaccharide gels in a process of hydrophobic interaction chromatography, for the absorption and desorption of the extractives in the presence of and as a result of the concentration and selection of an organic solvent.

BACKGROUND OF THE INVENTION

Agricultural plants, and waste streams from their processing, by way of an example, may contain components that are now being discovered as having desirable therapeutic and other benefits. For example: some saponins have been shown to exhibit antineoplastic chemotherapeutic value (U.S. Pat. No. 5,558,866), while others find use in the treatment of hypercholesterolemia (U.S. Pat. No. 5,502,038). Still further antifungal (e.g. Crombie, W. M. L., and Crombie, L., Phytochemistry 25: 2069–2073, 1986) and immunogenic (U.S. Pat. No. 5,597,807) activities are known as well as surfactant, emulsifying and foam stabilizing properties which are summarized by Price et al. (CRC Crit. Rev. Food Sci. Nutr., 26, 27–135, 1987). These are but a few examples from the literature.

In addition, some flavones and their glycosides are known to exhibit antimutagenicity (e.g. Peryt, B., et al., Mutation Res. 269: 201–215, 1992), and antitumor activity (e.g. Wei, H., et al., Cancer Res. 50: 499–502, 1990). Further reports of beneficial biological activities and functional properties can be found in a number of reviews (e.g. "Plant flavonoids in biology and medicine II. Biochemical, cellular, and medicinal properties" Ed. By V. Cody, E. Middleton Jr., J. B. Harborne, and A. Beretz, Liss Inc, New York, 1988.)

Canadian Patent Applications 2,006,957 and 2,013,190 describe ion-exchange processes carried out in aqueous ethanol to recover small quantities of high value byproducts from cereal grain processing waste. According to CA 2,013,190, an alcoholic extract from a cereal grain is processed through either an anionic and/or cationic ion-exchange column to obtain minor but economically valuable products. The anionic, cationic and neutral fractions were analysed by thin-layer chromatography and a number of components were identified. For example in an anionic fraction from an alcoholic extraction of hull-less whole oats, the following components were identified: phenolic acids, including ferulic acid, p-coumaric acid and caffeic acid; alkaloids such as avenanthramides; fatty acids, organic acids and amino acids. From the same alcoholic extract the neutral fraction contained compounds, such as: free sugars; phenolics, such as flavonoids; saponins such as avenacosides and desglucosyl-avenacosides; alkaloids such as the avenacins; and various polar lipids. The compounds identified in the various fractions were not individually isolated by ion-exchange chromatography since many carried the same net charge under the conditions used and thus, this method alone is of little value in the isolation of these useful components for industrial or commercial use. Furthermore, the extractives to be isolated in the present invention are for the most part neutral under conditions used, and thus cannot be isolated by ion exchange chromatography alone, which sorts molecules according to charge.

PCT application WO 92/06710, discloses both the composition and isolation/separation technologies of Quillaja saponins for end uses as immunogenic complexes, using repeated semi-preparative high performance liquid chromatography (HPLC) on a reverse-phase column with an acetonitrile:water gradient elution. The scale of the separation appears not to be intended for production of significant quantities for commercialization but rather for proof of efficacy. The isolated products were produced only on the microgram scale. The scale-up of the separation technique for commercial applications was not disclosed.

U.S. Pat. No. 5,094,960 describes methods of removal of process chemicals from labile biological mixtures by hydrophobic interaction chromatography (HIC) using a resin comprising octadecyl chains coupled to a silica matrix. A method of removing lipid soluble process chemicals such as synthetic detergents, chemical inducers and organic solvents from aqueous biological fluids, particularly directed to producing a protein-containing composition such as blood plasma, cryoprecipitates, and blood plasma fractions, was described. In this disclosure materials and conditions are employed that minimize adsorption and separation of proteins and maximize the removal of the process chemicals. Substantially no biological material is retained on the column. Furthermore, no indication is given as to the intended field of use of any of the compounds and chemicals adsorbed in the process, nor specific conditions to selectively recover any of the adsorbed components retained on the column.

A number of different procedures are known for the isolation and purification of isoflavones. D. E. Walter described a procedure for the preparation of the isoflavone genistin and its aglycone genistein from defatted soybean flakes (J. Amer. Chem. Soc. 63, 3273–3276, 1941). The procedure involved methanol extraction, acetone precipitation, centrifugations and several recrystallizations and gave only one isoflavone, genistin, from which the aglycone genistein could prepared by acid hydrolysis. Ohta et al. described a procedure for isoflavone extraction from defatted soybeans wherein the flakes were extracted with ethanol and the ethanolic extract treated with acetone and ethyl acetate. Column chromatography of the ethyl acetate fraction on silica gel and Sephadex LH-20™ in several additional solvents produced a number of fractions from which individual isoflavones could be recovered by repeated recrystallization (Agric. Biol. Chem. 43: 1415–1419, 1979). Essentially the same separation protocols were used by Farmakalidis, E. and Murphy, P. A. to separate isoflavones extracted using acidified acetone rather than ethanol (J. Agric. Food Chem. 33: 385–389, 1985). These publications are but a few of the many examples in the literature for the laboratory scale extraction and purifications of specific isoflavones. However due to issues of solvent handling and disposal as well as economic feasibility, these procedures are hard to scale up to a commercial process and produce single compounds in undisclosed yields.

U.S. Pat. No. 5,679,806 addressed some of these issues, disclosing a process for the isolation and purification of isoflavones from plant material. The process consisted of three steps whereby the plant material is extracted, the resulting extract fractionated on a reverse phase low pressure polymethacrylate or $C_{18}$ chromatography column by gradient elution of the adsorbed isoflavones from the column, and finally the resulting fractions containing specific isoflavones are eluted from the column. This process differs in several significant ways from the process described in the embodiments disclosed herein. First, the present process is not restricted to the isoflavone components but also yields a saponin fraction substantially free of isoflavones as well as the entire group of isoflavones which, if desired, can be further fractionated for individual components. Secondly, the present process does not rely on methacrylate or $C_{18}$-substituted reverse phase inorganic support matrices, which generally display much lower loading capacities and are harder to clean in place than polysaccharide-based gels. Thirdly, the flexibility of the present process allows that conditions be varied, either to capture the isoflavones by absorption or to allow them to elute through the column leaving other non-isoflavone components still absorbed, simply by varying the amount of water in an aqueous alcohol washing solution.

U.S. Pat. No. 5,482,914 teaches that agarose-based gels can be synthesized/modified for the binding of lipoproteins by covalently linking glycidyl ethers of polyoxyethylene detergents of the type $HO-(CH_2CH_2O)_n-O-R$ to give a modified gel matrix suitable for the removal of lipoproteins from human and animal body fluids. This technology refers only to the chemical processes for producing the gel and makes no claims either for electrostatic binding of ligands such as we describe, or for any examples of separation or recovery from plant material.

Thus, there is still a need for processes, chromatographic procedures and improved absorption media that are adaptable to a wide range of compounds in a commercially viable manner that provide high concentrations of these compounds which can be subsequently recovered in high yield, purity and in unaltered form. There is also a need for a process in which the chromatographic media can be regenerated and re-used many times to reduce both waste disposal costs and replacement costs. Furthermore, for commercial scale production of non-polar extractives it would also be advantageous to reduce the direct contact of solvents such as chlorinated hydrocarbons (e.g. chloroform, dichloromethane), nitriles (e.g. acetonitrile), aromatics (e.g. benzene, toluene), other potentially undesirable reagents (e.g. salts, mineral acids, bases), and chromatographic media contaminants (methacrylate-, divinylbenzene-, styrene-monomers, silica etc.) from direct contact with desired products. To accomplish this latter objective and still achieve the necessary separations, it would be desirable to selectively alter the chromatographic media to achieve the separation required and use only one simple, acceptable solvent, rather than to use a single chromatographic media and rely on a wide range of more unacceptable solvents. It is to these ends that this technology is directed.

SUMMARY OF THE INVENTION

The present invention relates to a process for the preparation of electrostatically-linked, aliphatic- or alicyclic-substituted anionic or cationic polysaccharide gels from readily available macroporous ionic polysaccharide chromatographic media.

The present invention also relates to the electrostatically-linked, aliphatic- or alicyclic-substituted anionic or cationic polysaccharide gels so produced.

The present invention further relates to the isolation, recovery and purification of non-polar extractives using said polysaccharide gels in a process of hydrophobic interaction chromatography, for the absorption and desorption of the extractives in the presence of and as a result of the concentration and selection of an organic solvent.

Thus, according to the present invention there is provided a method of preparing an electrostatically-linked, aliphatic or alicyclic-substituted anionic or cationic polysaccharide gel from a macroporous ionic polysaccharide chromatographic matrix comprising the steps of:

attaching, by ion exchange, a hydrophobic ligand containing a strongly ionizable functional group of opposite charge to that of the said polysaccharide, so that a substantial amount of the available ionic sites of the said polysaccharide are occupied by the ligand to form a modified hydrophobic phase component.

Further according to the present invention there is provided an electrostatically-linked, aliphatic- or alicyclic-substituted anionic or cationic polysaccharide gel comprising a hydrophobic ligand electrostatically bonded to a macroporous ionic polysaccharide gel matrix, so that a substantial amount of the available ionic sites of the said ionic polysaccharide gel matrix are occupied by the ligand to form a modified hydrophobic phase component, wherein the ligand contains a strongly ionizable functional group of opposite charge to that of the said ionic polysaccharide gel matrix.

This invention is also directed to a method of isolating a non-polar extractive comprising:

contacting said non-polar extractive in an aqueous organic solvent solution with a gel matrix selected from the group of an electrostatically-linked, aliphatic- or an alicyclic-substituted anionic or cationic polysaccharide gel matrix;

washing said gel matrix with said aqueous organic solvent solution;

washing said gel matrix with additional aqueous organic solvent solution, wherein the proportion of the solvent in said additional solution is increased; and recovering said extractive from an effluent stream.

BRIEF DESCRIPTION OF THE DRAWINGS

These and other features of the invention will become more apparent from the following description in which reference is made to the appended drawings wherein:

FIG. 7a shows the TLC profile of quinoa enriched saponin fraction. FIG. 7b shows the TLC profile of the quinoa Group 1 saponin fraction and FIG. 7c shows the TLC profile of the quinoa Group 2 saponin fraction.

DESCRIPTION OF PREFERRED EMBODIMENT

Figure 1:
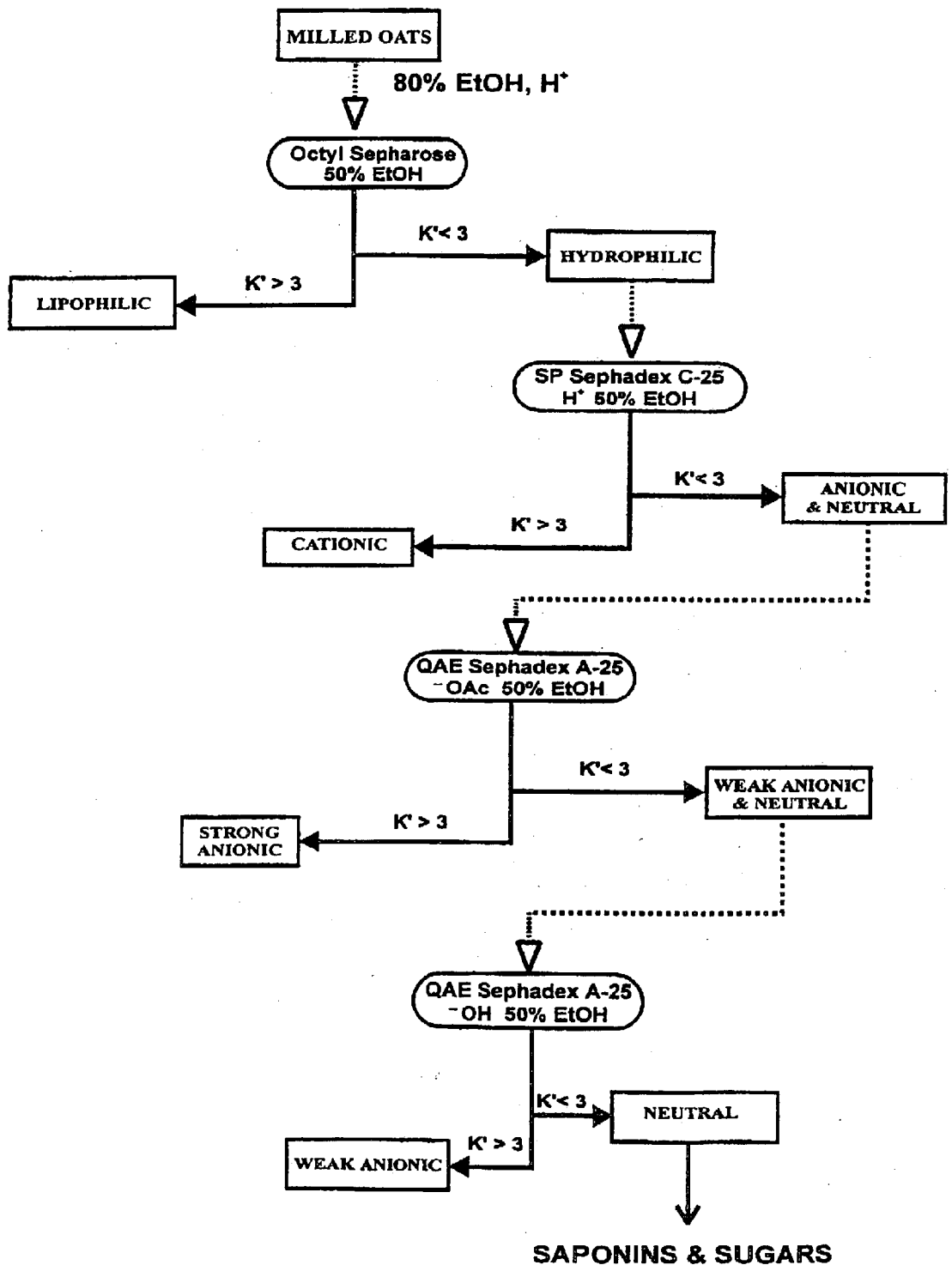
FIG. 1 shows the extraction and group separation of oat saponins.

The present invention relates to a process for the preparation of electrostatically-linked, aliphatic- or alicyclic-substituted anionic or cationic polysaccharide gels from readily available macroporous ionic polysaccharide chromatographic media. The present invention further relates to the isolation, recovery and purification of non-polar extractives using said polysaccharide gels in a process of hydrophobic interaction chromatography, for the absorption and desorption of the extractives in the presence of and as a result of the concentration and selection of an organic solvent.

The fundamental principles of both hydrophobic interaction chromatography (HIC) and reverse phase chromatography (RPC) are similar: chromatographic separation of components of a mixture based on their differential affinities between a non-polar or hydrophobic ligand attached to a stationary phase, and a mobile phase. In RPC, the stationary phase usually, but not always, consists of an inorganic, pelliculate or particulate, hydrophilic support, typically silica, onto which a specific ligand with a relatively high degree of hydrophobicity has been introduced at a complete or extremely high substitution rate to effectively replace, mask or resurface the hydrophilic stationary phase. The mobile phase usually, but not always, contains an organic modifier (i.e. organic solvent) typically methanol, acetonitrile, or tetrahydrofuran. In HIC, the stationary phase typically consists of an organic, hydrophilic, macroporous support, typically a chemically modified polysaccharide or polyacrylamide, onto which a specific ligand with a relatively low degree of hydrophobicity, has similarly, but usually to a much lower substitution rate, been introduced to modify but not necessarily eliminate the hydrophilic properties of the support. The mobile phase usually, but not always, consists of water containing a buffer or salt solution of variable concentration.

RPC is now the most commonly used technique for high performance liquid chromatography (HPLC) separation of relatively stable low molecular weight organic compounds. However, separation of many biological macromolecules (e.g. proteins, peptides and nucleic acids) by RPC has found only limited application, because the stronger interaction with a highly hydrophobic stationary phase and the use of organic solvents as eluent constituents can be very detrimental to the native structure of the macromolecules. As a result of these interactions, most of the macromolecules are subjected to unfolding and denaturation with the concomitant loss of some or all of their biological activity.

HIC has developed as a practical alternative to RPC for the separation and purification of biological macromolecules because both the absorption and desorption processes can be carried out in an aqueous buffer by simply varying the salt concentrations, conditions that are more favorable to the retention of biological activity of the macromolecule. However, few applications of HIC for the separation of low molecular weight, relatively stable organic compounds appear to have been made. In accordance with the present invention, by maintaining a functional hydrophilic core in addition to the hydrophobic ligand in close spacial proximity, the HIC stationary phase displays unique advantages for the separation and purification of amphiphiles (i.e. compounds containing both hydrophilic and hydrophobic regions) not available in most if not all RPC stationary phase chromatographic media. Examples of such amphiphilic extractives, include but are not limited to saponins, flavonoids and prolamines, which contain hydrophilic substituents (i.e. glycosidic residues) attached to a relatively non-polar backbone. If these amphiphiles additionally show stability towards certain organic solvents such as the lower alcohols and ketones, including ethanol, isopropanol and acetone, these solvents can be used to recover the components bound to the gel (i.e. running the HIC system in an "RPC mode") by either gradient, sequential or batch recovery techniques known by the person skilled in the art of chromatography.

Furthermore, according to the present invention we have observed that such HIC gels possess the capacity to clarify aqueous dispersions and micelles known to be formed when such amphiphiles (i.e. aqueous solutions and dispersions of saponins, flavonoids and prolamines above their critical micellar concentration) are produced artificially or encountered in the extraction, concentration and purification or other manipulation of aqueous alcoholic preparations from agricultural plants and co-processing streams.

The hydrophobic interaction chromatography polysaccharide gel of the present invention can consist of a cationically substituted polysaccharide gel matrix made from a neutral polysaccharide of the polyanhydrogalactan or polydextran class such as crosslinked agarose, containing covalently-linked cationically-charged functional groups such as tertiary amines (DEAE, PEI) or quaternary amines (QAE, Trimethylamine) such as DEAE Sephadex A-25™ (diethlaminoethyl polydextran), QAE Sephadex A-25™ (quaternary aminoethyl polydextran) and Q Sepharose™ (quaternary amine crosslinked agarose) (Amersham Pharmacia Biotech., Piscataway, N.J.). According to this embodiment of the present invention these gels are modified by a hydrophobic ligand. The ligand is selected from an anionically-linked alkyl substitution of the class of anionic detergents including alk(en)yl sulfonates and sulphates, alk (en)yl phosphonates and phosphates, mono- and di-alky(en) ylphosphatidic acids. Said ligand can also include an anionically-linked alicyclic substitution of the class of anionic detergents including taurocholates and taurodeoxycholates or by mixed ligands of the class of anionic detergents including alk(en)yl-arylsulfonates such as dodecylbenzenesulfonic acid and alk(en)ylbenzenesulfonates. According to this aspect of the invention the alk(en)yl substitution contains from about 4 to about 18 carbons.

The hydrophobic interaction chromatography polysaccharide gel can also consist of an anionically substituted polysaccharide gel matrix made from a neutral polysaccharide of the polyanhydrogalactan or polydextran class such as cross-linked agarose, containing covalently linked anionically charged functional groups such as alk(en)yl sulfonates and alk(en)yl phosphonates. Specific examples include sulfopropyl (SP) such as SP Sephadex C-25™ (sulfopropyl polydextran) (Pharmacia, Piscataway, N.J.). S Sepharose™ (methyl sulfonate crosslinked agarose) is a further example of the polysaccharide gel matrix according to this embodiment of the invention. According to this embodiment of the present invention these gels are modified by a hydrophobic ligand. In this embodiment the hydrophobic ligand is a cationically-linked alkyl substitution of the class of cationic detergents including alk(en)yltrimethylammonium halides such as CETRIMIDE™ (Sigma Chemical Co., St. Louis, Mo.) and quaternary alk(en)ylammonium halides such as tetrabutylammonium bromide (Sigma Chemical Co., St. Louis, Mo.), quaternary alk(en)ylpyridinium halides such as hexadecylpyridinium bromide, or alk(en)ylmagnesium halides and similar Grignard reagents. According to this aspect of the invention the alk(en)yl substitution contains from about 4 to about 18 carbons.

Thus, the present invention involves the production of specific HIC gels from readily available starting materials by simple ion exchange procedures as described herein. Basically, either of the two different types of ion exchangers, anionic or cationic, preferably consisting of an ionically-substituted polysaccharide gel, can be used as the hydrophilic core. To this core a hydrophobic ligand, chosen from the aforementioned classes of anionic or cationic detergents and containing a strongly ionizable functional group of opposite charge to that of the polysaccharide, is attached by ion exchange so that all, or substantially all, of the available ionic sites in the original polysaccharide are occupied by the ligand to form a modified, hydrophobic phase component. By the term "all or substantially all" it is meant that at least 70% of the available ionic sites in the original polysaccharide are occupied by the ligand and can include up to at least 90% of the available ionic sites.

As an example of the process of preparation of these novel gels, QAE Sephadex A-25™ anionic exchange chromatography gel, in the chloride form as received from the manufacturer and equilibrated in aqueous ethanol, for example aqueous 50% ethanol, was gravity packed into a column. The solvent need not necessarily be aqueous ethanol but any such solvent as water, or aqueous methanol, isopropanol or acetone containing sufficient water to effect swelling of the polysaccharide core matrix-would be effective for the purpose of the present invention. The column is first converted to the hydroxide (i.e. $OH^-$) form. In one example this step is accomplished by passing an excess of hydroxide ion equivalents (for the quantity of gel being prepared) of a dilute base through the column and then washing the column to neutral pH. In one example the dilute base is a 0.5N solution of NaOH in aqueous 50% ethanol and the washing solution is also aqueous 50% ethanol. The base need not necessarily be NaOH but any base such as KOH, $NH_4OH$, etc. and, as outlined above, the solvent need not necessarily be aqueous 50% ethanol. The column is then converted to the desired novel anionic detergent substituted form by simply passing excess ionic equivalents of that detergent through the column and again washing the column to remove any excess detergent. In one example the anionic detergent is 0.5N sodium dodecyl sulfate (SDS) in aqueous 50% ethanol and the washing solvent is also aqueous 50% ethanol. This procedure is essentially the same for any of the aforementioned anionic detergents, and would be familiar to any person skilled in the art of ion exchange chromatography.

As another example of the process for the preparation of these novel gels, SP Sephadex™ C-25 cationic exchange chromatography gel, in the sodium form as received from the manufacturer and equilibrated in aqueous ethanol, for example aqueous 50% ethanol, was gravity packed into a column. The solvent need not necessarily be aqueous ethanol but any such solvent as water, or aqueous methanol, isopropanol or acetone containing sufficient water to effect swelling of the polysaccharide core matrix. The column is first converted to the hydrogen (i.e. $H^+$) form. In one example this step is accomplished by passing an excess of hydrogen ion equivalents (for the quantity of gel being prepared) of a dilute acid through the column and then washing the column to neutral pH. In one example the dilute acid is a 0.1N solution of HCl in aqueous 50% ethanol and the washing solution is also aqueous 50% ethanol. The acid need not necessarily be HCl but any acid such as $H_2SO_4$, trifluoracetic acid, $H_3PO_4$, etc. and, as outlined above, the solvent need not necessarily be aqueous 50% ethanol. The column is then converted to the desired novel cationic detergent substituted form by simply passing excess ionic equivalents of that detergent through the column and again washing the column to remove any excess detergent. In one example the cationic detergent is 0.5N hexadecyltrimethylammonium ($HDTMA^+$) bromide in aqueous 50% ethanol and the washing solvent is also aqueous 50% ethanol. This procedure is essentially the same for any of the aforementioned cationic detergents, and would be familiar to any person skilled in the art of ion exchange chromatography.

The use of these cationically substituted and anionically substituted polysaccharide gels opens a whole new area of selective hydrophobic interaction separation technologies allowing the user to select an appropriate ionic counterion for attachment to the gel for specific applications e.g. for the isolation of steroids one would use taurocholic acid, or cholesterol sulfonate to bind estrogens, sex hormones etc.; one would use cis vs trans unsaturated alkyl groups to separate isomer mixtures for health food ingredients, to mention only a few possibilities. A person skilled in the art of chromatography will readily recognize other similar gels, which can be prepared for specific applications.

As mentioned previously, the present invention also relates to the use of these gels for the isolation, recovery and purification of non-polar extractives. This aspect of the invention depends on the hydrophobicity of the non-polar extractives to be isolated and the change in hydrophobicity that results from altering the concentration of the recovery solvents, which can be achieved by adding more or less water to the recovery solvent. More specifically, this embodiment of the present invention is based on the observed selective differences in the hydrophobic attraction between relatively non-polar extractives containing aliphatic and/or alicyclic functional groups, as compared to those containing aromatic and/or olefinic functional groups, or neither; and an aliphatically- or alicyclically substituted polysaccharide-based gel; and on the changes in this attraction that can be made by altering the composition of suitable solvents, simply by the addition of more or less water.

By non-polar extractives, it is meant that the extractives are only partially soluble in aqueous alcoholic solvents ranging in composition from 5% to 95%. This term includes extractives that are relatively non-polar. In one aspect of the present invention the groups of compounds that can be separated are non-polar compounds and are selected from the group, but are not limited to: steroids and triterpenoid derivatives, such as saponins, cardiac glycosides and steryl conjugates; flavonoids, such as flavones, flavonols, isoflavones and all of their glycosides; phenolic conjugates, such as aliphatic alcohol esters and amides; polar lipids, such as mono- and di-glycerides and their derivates and alk(en)ylresorcinols; and prolamines, such as zein, avenin, hordein or gliadin. The non-polar compounds of the present invention include both naturally occurring compounds and synthetic compounds.

By synthetic compounds it is meant any compound prepared by synthetic chemical means. The method of the present invention is particularly useful for the purification of synthetic compounds which have pharmaceutical or therapeutical value.

Naturally occurring compounds include the compounds referred to above, and also include compounds from algae, fungi and unicellular organisms. These naturally occurring compounds include compounds naturally occurring in the microorganism and also those produced by genetically altered cells.

In one embodiment of the present invention the novel gels are used to isolate and purify saponins from different sources. Saponins are sapogenols (triterpenoid aglycones) containing up to five sugars. Saponins in general and soyasaponins in particular are gaining much attention because of the growing market share of soybeans and also from a pharmacological standpoint. Soyasaponins have been reported to exhibit haemolytic, goitrogenic, antioxidative and hypolipidemic properties. They have also been shown to impart a bitter and astringent taste to soy-based foods. Their isolation and characterisation is important for the breeding of new varieties and for their production as pharmacologically active value-added products. However, because of their complex chemistry, known chemical isolation techniques (i.e., saponification or solvent extraction) may yield low quantities or hydrolysed products.

In one example, the present invention was used for the isolation of oat saponins. Two different types of saponins have been isolated from oat kernels: the avenacoside-type pentacyclic triterpenoid saponins and the avenacin-type steroidal saponins. Both types show selective antimicrobial activity (e.g. Wubben, J. P., et al., Phytopath. 86, 986–992, 1996; Maizel, J. V., et al., Biochemistry 3, 424–426, 1964) and may prove valuable as active ingredients in topical creams and lotions for health care products or as antimicrobials for agricultural seed dressing formulations.

In another embodiment of the present invention, the novel gels were used for the isolation of saponins from quinoa. *Chenopodium quinoa* Willd. (quinoa) is a grain native to South America. Much scientific interest has been generated in recent years due to the grain's nutritional value (the protein content averaging 14% fresh weight) and its hardy growing characteristics. Unfortunately, the grain has had limited use as a human food source because of the bitterness of the seed coat, which is thought to be caused in part by the presence of saponins. These saponins are primarily found in the outer layers of the grain including the perianth and pericarp. Traditionally, the grain has been washed with water to remove most of these bitter components, prior to consumption.

In the past decade, nearly two dozen saponins, both neutral and acidic have been isolated from quinoa (e.g. Mizui, F., et al., Chem. Pharm. Bull. 36: 1415–1418, 1988; Mizui, F., et al., Chem. Pharm. Bull. 38: 375–377, 1990). These saponins contain one of three pentacyclic triterpene algycones; oleanolic acid, hederagenin or phytolaccagenic acids. The glycosidic moieties of the neutral saponins can consist of any combination of glucose, galactose, or arabinose, producing mono, di, tri and tetraglycosides. The acidic saponins may contain acidic functionalities at C-28, or a glucuronic acid residue attached to C-3 of the triterpenoid backbone. In general, these saponins are fairly polar containing up to four glycosyl residues. Both diacids and bisdesmosides have been isolated.

Recently, quinoa saponins have been used in pharmaceutical preparations as immunological adjuvants (e.g. U.S. Pat. Nos. 5,597,807 and 5,688,772). They have been shown to stimulate nonspecific immunity, enhance an immunological response to a selected antigen and enhanced mucosal absorption of an administered drug.

Methods to isolate saponins from quinoa have involved the extraction of whole seed or bran fractions by either water or methanol (e.g. Ridout, C., et al., J. Sci. Food Agric. 54: 165–176, 1991, and Meyer, B. N., et al., J. Agric. Food Chem. 38: 205–208, 990). In both procedures, the extracts are defatted by a non-polar solvent such as petroleum ether or diethyl ether. Solvent partition (usually n-butanol/water) followed by classic column chromatography using silica gel with methanol/chloroform has resulted in the isolation of these compounds. These methods would be difficult to commercially develop due to the use of harsh solvents, incomplete partitioning of components and variability in yields. A number of chemical, spectral, enzymatic and bioassay directed methods to detect quinoa saponins have been reported in the literature including GC (e.g. Burnouf-Radosevich, M., et al., Phytochemistry 24: 2063–2069, 1984), HPLC (e.g., Ruales, J., and Nair, B., Food Chemistry 48: 137–143, 1993), and TLC (e.g. Ng, K. G., et al., Food Chemistry 49: 311–315, 1994). Individual saponins have been characterised by NMR and GC-MS (e.g. Ma, W-W., et al., J. Nat. Prod. 52, 1132–1135, 1989).

In one embodiment of the present invention, the compounds can be isolated from plant material. The term plant material includes products of agriculture, viniculture, horticulture or aquaculture. Agricultural plants include cereal grains, for example wheat, oats, rye, corn, rice, quinoa, amaranth, buckwheat, triticale or barley; or oilseeds, such as soybean, canola, flaxseed, sunflower, safflower or mustard; or pulsecrops, for example, peas, lentils or beans; or forage crops, such as fescue, timothy, clover, alfalfa or wheatgrass; or herbs, such as parsley, rosemary, sage, or mint. The compounds can also be recovered from their co-processing streams. However, the invention is not limited to compounds isolated from plants or agriculture co-processing products. The invention can also be used to extract compounds from algae, fungi and unicellular organisms.

The washing solvents, extracting solvents, or recovery solvents, in the context of the present invention these terms are interchangeable, can include but are not limited to the lower alcohols such as methanol, ethanol, propanol or isopropanol; ketones, such as acetone; water, and a combination of the lower alcohol, or ketone, with water.

A person skilled in the art of extraction of naturally-occurring plant constituents will recognize that a number of different extractions methods exist in the literature, including percolation, vat extraction, counter-current extraction, etc. The particular method of extraction used is not important to the process of the present invention.

The present invention uses hydrophobic interaction chromatography alone or in combination with other separation techniques to isolate the compound of interest. In this respect, the invention defined in the present application can be combined with the separation techniques defined in Applicant's co-pending application entitled "A Process for the Purification of Non-Polar Extractives", which uses aliphatic-substituted polysaccharide gel matrices in a process of hydrophobic interaction chromatography.

The process of purifying the non-polar extractive, according to the present invention involves three basic steps: absorption, washing and recovery. According to one aspect of the present invention, the process involves a fourth optional step of regenerating the column, without the use of a harsh chemical treatment or the generation of excessive salt or non-recoverable processing waste stream.

According to the present invention, separation and purification of a wide range of extractives with similar solubilities in aqueous alcoholic solvents can be effected based on their differential binding to specifically-modified polysaccharide gels. Such extractives can include: steroids and triterpenoids, such as saponins, cardiac glycosides and steryl conjugates; flavonoids, such as flavones, flavonols, isoflavones and all of their glycosides; phenolic conjugates, such as aliphatic alcohol esters and amides; polar lipids, such as mono- and di-glycerides and their derivatives and alk(en)ylresorcinols; and prolamines, such as zein, avenin, hordein or gliadin.

In establishing whether a compound is considered to be bound to the gel and to have exhibited hydrophobic interaction with the gel, the following criteria must be met:
a) it must be soluble in, or form a micelle or stable emulsion in, the solvent with which it is loaded onto the column, and with which the column is washed; and
b) it must be retained by the gel after washing with at least $1.25 \times V_b$ of the washing solvent, wherein $V_b$ is the packed bed volume of the column; wherein the washing solvent is a lower alcohol in combination with water in a ratio sufficient to retain said compound.

This latter criterion must be met since porous gels of the types described herein show molecular size exclusion capabilities. These effects are not however observed beyond approximately $1.25 \times V_b$ and therefore are not involved in the processes or practices described.

In the recovery step, the proportion of the organic solvent in the elution aqueous organic solvent is increased to decrease the hydrophobic binding of the extractive to the gel and thus elute the extractive. In some embodiments of the present invention the extractive can be eluted with the initial washing stream.

In the present invention, reference will be made to the degree of relative hydrophobic interaction of specific compounds or groups and/or classes of compounds by the use of a dimensionless constant, K' defined as the ratio of the number of mL of a particular solvent to move the compounds through a volume of 1 mL of gravity packed gel. Since this dimensionless constant is independent of column dimensions (i.e. length, diameter, etc.), the conditions described herein can be used for scaled up operations over several magnitudes.

As noted previously, an optional fourth step of the present invention is the regeneration of the column, without the use of any harsh chemicals or the generation of excessive salt or non-recoverable processing waste stream. Since conditions for each application have been established wherein the compounds of interest have been totally removed from the gel, the column can be regenerated and re-equilibrated in the starting solvent. Surprisingly, it has been found that a simple washing of the gels with a suitable solvent such as 95% ethanol or isopropanol is sufficient in most cases to remove any material appearing to be adhering to the gels at the end of a process application. The gels are then re-equilibrated with starting solvent for immediate reuse. In this manner, regeneration and recycling up to at least 4000 times over 10 years have been observed without noticeable loss of effectiveness in the processes described herein. Clean-in-place/sanitation procedures where deemed appropriate can be effected using dilute NaOH as per manufacturers recommendations (Amersham Pharmacia Biotech manuals, technical bulletins, etc.).

The purification of the compound, according to the present invention, can be carried out at any suitable temperature, known to persons skilled in the art. The column separations can be accomplished at temperatures ranging from about 2° C. to 60° C. Temperature ranges from about 4° C. to 30° C., being more commonly used.

While this invention is described in detail with particular reference to preferred embodiments thereof, said embodiments are offered to illustrate but not to limit the invention.

EXAMPLES

Example 1

Isolation of Oat Saponins from Oat Flour Using Hydrophobic Interaction Chromatography on Octyl Sepharose CL-4B™ and Novel Substituted Hydrophobic Gels Two different types of saponins have been isolated from oat kernels: the avenacoside-type pentacyclic triterpenoid saponins and the avenacin-type steroidal saponins. The structures of two avenacosides, avenacoside A and avenacoside B have been elucidated (Tschesche, R., et al., Chem. Ber., 102, 2072–2082, 1969; Tschesche, R. and Lauven, P., Chem. Ber., 104, 3549–3555, 1971), but at least 2 other avenacosides remain uncharacterized (Kesselmeier, J. and Strack, D., Z. Naturforsch. 36C, 1072–1074, 1981). Several of the avenacin-type saponins have also been structurally identified (Crombie, L., et al., J. Chem. Soc., Perk. Trans. 1, 1917–1922, 1986).

In the case of the avenacosides A and B, the steroid moiety is glycosylated with a total of 5 and 4 sugar residues respectively, while the 4 avenacins are the same trisaccharide derivative of 4 similar but not identical sapogenols. The co-occurrence of such complex mixtures of neutral saponins makes their separation difficult either as groups or individual components, from extracts which contain sugars and oligosaccharides of similar composition. In the following example, extensive use was made of hydrophobic interaction chromatography to first allow group separation of the saponins and secondly, to facilitate the purification of specific components of each type of saponin.

First, HIC on Octyl Sepharose CL-4B™ in aqueous 50% ethanol was utilized to carry out a group separation of all the oat saponins of both types, amongst others, from polar and non-polar non-saponin components. Then all the oat saponins were further purified as a group by removing charged components from this saponin-containing fraction by cation exchange chromatography on SP Sephadex C-25™ in the hydrogen form and double anion exchange chromatography on QAE Sephadex A-25™ in the acetate and hydroxyl forms, as described below. Since the oat saponins are uncharged, they will not be absorbed by any of these steps and will pass through all three types of columns along with other neutral components. Finally, HIC on both Octyl Sepharose CL-4B™ and SP Sephadex C-25™ in the hexadecyltrimethylammonium (HDTMA$^+$) form were used to separate the avenacin saponins from the avenacoside saponins and to purify individual members of these two groups. It should be emphasized that during the saponin purification processes described below, a number of non-saponin fractions were also generated that were highly enriched in other components. Since the methods described herein involved ethanol and water as the only solvents, and volatile acids and bases as the only reagents, these fractions represent excellent sources for additional values.

Thus, a sample of *Avena saliva* L. cult. Tibor was milled to pass through a 1 mm screen and 25 g of the resulting oat flour added with vigorous stirring to 125 mL (solids/liquids= 1/5) refluxing acidified aqueous 80% ethanol (ethanol:water:glacial acetic acid 80:19:1 v:v:v). The mixture was heated for an additional 20 minutes with continuous stirring under reflux. After cooling to approximately 4° C., the resuspended mixture was transferred to a volumetrically graduated glass column fitted with a coarse porosity fritted disk, and allowed to warm to room temperature (25° C.) and settle by gravity to give a packed bed of known volume ($V_b$). The column was then drained and washed with $2 \times V_b$ fresh acidified aqueous 80% ethanol, and this percolation-type extraction process repeated twice. After draining, the extracted solid residue was removed from the percolation extraction column and air-dried to constant weight to determine the percentage of oat flour extracted. The extracts and washings were combined and were concentrated in vacuo to an oily syrup by rotary evaporation at 40° C., and represented 16% by weight of the original oat groats. The oily syrup was then dispersed in aqueous 80% ethanol, 5 mL of Octyl Sepharose CL-4B™ beads in aqueous 80% ethanol added, and the mixture evaporated to a thick slurry in vacuo by rotary evaporation at 40° C. The slurry was then resuspended in aqueous 50% ethanol and transferred to a graduated column of 45 mL Octyl Sepharose CL-4B™, pre-equilibrated and gravity packed in the aqueous 50% ethanol solvent. The column (final $V_b$ 50 mL) was then washed with $3 \times V_b$ of the same solvent, to give a washings fraction with $K' \leq 3$ containing all the oat saponins, sugars, amino acids, and salts amongst others, and a $K' \geq 3$ fraction, still hydrophobically bound to the gel. This $K' \geq 3$ fraction, containing carotenoid pigments, acyl glycerides, polar lipids, some of the oat prolamines and free sterols amongst others, was recovered and the gel recycled by first passing $2 \times V_b$ of aqueous 95% ethanol through the column to recover the bound material, and then $2 \times V_b$ of re-equilibrating solvent.

Thus the $K' \leq 3$ fraction prepared above was first treated to remove components such as cationic prolamines, peptides, amino acids and inorganic cations, by chromatography on SP Sephadex C-25™ in the hydrogen form. Accordingly, a volumetrically graduated column containing 50 mL (=$V_b$; i.e. 2 mL gel/gm oat groats extracted) of SP Sephadex C-25™ in the sodium form (as received from the manufacturer) was swollen in aqueous 50% ethanol and converted to the hydrogen form by treating the column, with a 3-fold milli-equivalent excess of 0.1N HCl in aqueous 50% ethanol, and washing the column until the washings were pH ~6. The $K' \leq 3$ fraction prepared above and dissolved in 5 mL of aqueous 50% ethanol was then loaded onto the column and the column washed with $3 \times V_b$ of fresh aqueous 50% ethanol. The washing (i.e. $K' \leq 3$ fraction) containing the oat saponins, amongst others, was evaporated to dryness in vacuo by rotary evaporation at 40° C. This $K' \leq 3$ fraction was then treated to remove components such as anionic prolamines, peptides, and amino acids, organic acids and inorganic anions, all of which carry a net negative charge at or below pH 6. Accordingly, a 50 mL (=$V_b$; i.e 2 mL gel/gm oat groats extracted) QAE Sephadex A-25™ anion exchange column in the chloride form (as received from the manufacturer) was swollen in aqueous 50% ethanol and first converted to the hydroxyl form by treating the column with a 3-fold milliequivalent excess of 1.0N NaOH in aqueous 50% ethanol and washing the column until the washings were pH ~8. The column was then converted to the acetate form by treating the column with a 3-fold milliequivalent excess of 1% (v:v) glacial acetic acid in aqueous 50% ethanol and washing the column with aqueous 50% ethanol until the washings were pH ~6. The saponin-containing fraction in 5 mL of aqueous 50% ethanol was then loaded onto the column and the column washed with $3 \times V_b$ of fresh aqueous 50% ethanol. The washing (i.e. $K' \leq 3$ fraction) containing the oat saponins, amongst others, was evaporated to dryness in vacuo by rotary evaporation at 40° C. Finally, to remove the flavonoids, phenolics and other non-saponins carrying a net negative charge at pH ~8, the saponin fraction was passed through a 50 mL (=$V_b$; i.e 2 mL gel/gm oat groats extracted) QAE Sephadex A-25™ column anion exchange column in the hydroxyl form, prepared as described above. The saponin-containing fraction in 5 mL of aqueous 50% ethanol was then loaded onto the column and the column washed with $3 \times V_b$ of fresh aqueous 50% ethanol. The washings (i.e. $K' \leq 3$ fraction) containing primarily the oat saponins, galactoglycerides, neutral amino acids and sugars were concentrated in vacuo by rotary evaporation at 40° C. The preliminary fractionation scheme is summarized in FIG. 1.

Preliminary TLC examination of this $K' \leq 3$ fraction, as described below, showed the presence of a number of different coloured spots with the p-anisaldehyde detecting reagent including brown (free sugars), green (avenacoside-type sapogenins), grayish-blue (avenacin-type saponins), purple (galactosylglycerides) and yellow(lysophosphatides).

Hydrophobic interaction chromatography on Octyl Sepharose CL-4B™ and SP Sephadex C-25™ in the hexadecyltrimethylammonium (HDTMA$^+$) form were also used to separate the non-saponin components, to separate the avenacin saponins from the avenacoside saponins and to isolate individual members of these two groups from each other employing the following series of protocols. First the non-saponins and minor sapogenin mono- and di-glycosides were separated from the avenacins and avenacosides on Octyl Sepharose CL-4B™. The individual avenacins were then separated by further chromatography on Octyl Sepharose CL-4B™, and individual members of the more polar avenacosides, on SP Sephadex C-25™ in the HDTMA$^+$form. However, in order to isolate and identify individual components of the oat saponin mixture, an additional oat sample (100 g) was processed by scaling up the above procedure using the same column types, solvents and proportions. In this way a further approximately 300 mg of freeze-dried saponins were produced in a single run.

Thus, an aliquot (266.5 mg) of the freeze-dried saponins was dissolved in 10 mL acidified aqueous 40% ethanol (i.e. ethanol:water:glacial acetic acid 40:59.9:0.1 v:v:v). The solution was absorbed onto a 100 mL column (=$V_b$; 2.66 mg saponin/mL gel) of Octyl Sepharose CL-4B™, equilibrated and gravity packed in the same solvent. The column was washed with $2 \times V_b$ of fresh acidified aqueous 40% ethanol to give a $K' \leq 2$ sub-fraction which was evaporated to dryness in vacuo by rotary evaporation at 40° C. The column was then eluted with $2 \times V_b$ of aqueous 80% ethanol, to recover absorbed components and this sub-fraction (i.e. $K' \geq 2$ sub-fraction) similarly evaporated to dryness in vacuo by rotary evaporation at 40° C. TLC examination of the $K' \leq 2$ sub-fraction showed several blue fluorescent spots under long wave UV (365 nm) typical of the avenacins containing the N-methylanthraniloyl moiety, at least 4 green spots typical of the avenacosides when sprayed with the p-anisaldehyde reagent, and a large zone of high $R_f$ corresponding to the sugars and neutral amino acids amongst others. The $K' \geq 2$ sub-fraction by TLC examination contained a blue fluorescent spot at the origin under long wave UV (365 nm) typical of the aglycone of the N-methylanthraniloyl-containing avenacin sapogenol and both purple and yellowish spots, characteristic of certain classes of lipids when sprayed with p-anisaldehyde reagent as noted above. Thus, this first step effected the separation of both avenacin-type saponins and avenacoside-type saponins, recovered in the K'≦2 sub-fraction, from non-saponins (i.e. K'≧2 sub-fraction).

The next step involved the separation of the avenacin-type saponins from the avenacoside-type saponins and other remaining non-saponin components, by taking advantage of lower degree of glycosylation of the avenacins relative to the avenacosides and therefore their greater hydrophobic binding potential. Accordingly, the K'≦2 sub-fraction was dissolved in 10 mL acidified aqueous 20% ethanol (i.e. ethanol:water:glacial acetic acid 20:79.9:0.1 v:v:v) and absorbed onto a 100 mL column (=$V_b$) of Octyl Sepharose CL-4B™, equilibrated and gravity packed in the same solvent. The column was washed with 2x$V_b$ of fresh acidified aqueous 20% ethanol to give a K'≦2 sub-fraction which was evaporated to dryness in vacuo by rotary evaporation at 40° C. Components still absorbed on the column were then recovered using 2x$V_b$ of aqueous 80% ethanol, and this sub-fraction (i.e. K'≧2 sub-fraction) similarly evaporated to dryness in vacuo by rotary evaporation at 40° C. TLC examination of the 2 sub-fractions revealed that the K'≦2 sub-fraction contained the avenacosides along with the free sugars and neutral amino acids amongst others, but no detectable avenacins, while the K'≧2 sub-fraction contained the avenacins (i.e. the "avenacin sub-fraction') along with traces of low $R_f$ avenacosides.

Figure 2:
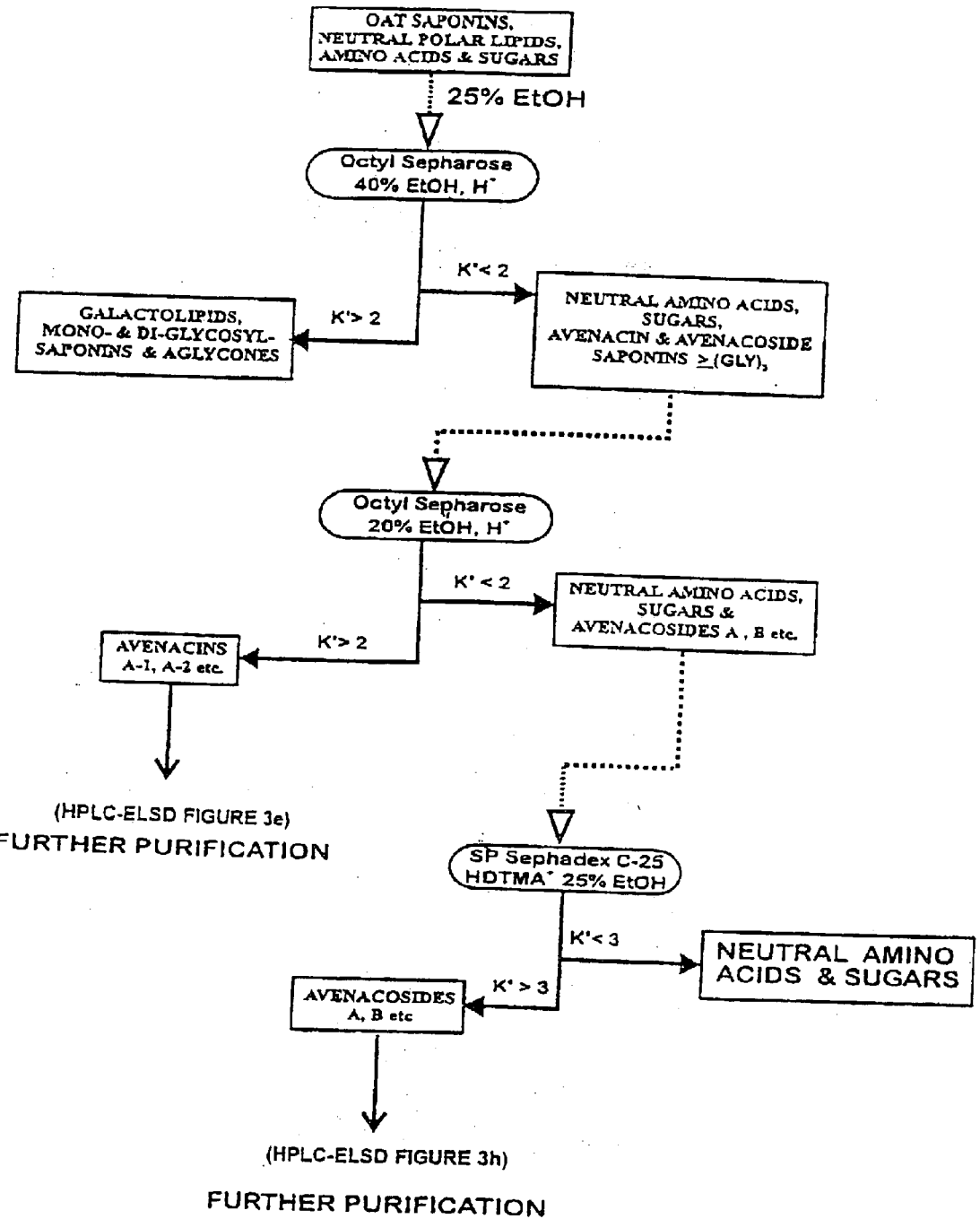
FIG. 2 shows the separation of avenacin-type and avenacoside-type oat saponins.

Finally, to remove the neutral amino acids and sugars from the avenacosides, the K'≦2 sub-fraction was chromatographed on a gravity packed 25 mL (=$V_b$; i.e 1 mL gel/gm oat groats extracted) SP Sephadex C-25™ in the hexadecyltrimethylammonium (HDTMA⁺) form, prepared as described above. Thus, the K'≦3 fraction in 5 mL of aqueous 25% ethanol was absorbed onto the column and washed with 3x$V_b$ of fresh aqueous 25% ethanol to give a K'≦3 sub-fraction devoid of saponins (TLC). The saponins absorbed on the column were then recovered with 3x$V_b$ of aqueous 80% ethanol, evaporated to dryness in vacuo by rotary evaporation at 40° C., and freeze-dried to an off-white powder (i.e. the "avenacoside sub-fraction"; yield: 77.5 mg; 0.31% dry basis). The flow diagram for the separation and recovery of the 2 major oat saponin types is summarized in FIG. 2.

Thin Layer Chromatography (TLC)

TLC of saponins was performed on MKC$_{18}$F reverse phase plates (1x3 in., 200 μm thickness, Whatman International Ltd, Maidstone, UK) using the solvent system methanol:aqueous 5% acetic acid (75:25 v:v)(i.e. methanol:water:glacial acetic acid 75:23.5:1.5 v:v:v). Compounds were visualized by spraying with a 0.5% solution (v:v) of p-anisaldehyde in acidified aqueous ethanol (i.e. ethanol:concentrated sulfuric acid:water:p-anisaldehyde 90:5:4.5:0.5 v:v:v:v) and heating at 100° C. for 3 min. This reagent gives a number of distinct colors with different constituents including brown (free sugars), transitory yellow quickly turning to pink, green, or grayish-blue (saponins), slowly appearing reddish (amino acids, prolamines), purple (galactosylglycerides), and yellow (lysophosphatides).

High Performance Liquid Chromatography (HPLC)

HPLC analyses of saponins were conducted using a Thermo Separations Products solvent delivery system and data collecting software (PC 1000) on a C$_{18}$ CSC Hypersil column (250x4.6 mm, 120 Å, 5 μm). A "mass detector" (evaporative light scattering detector, ELSD, Alltech Varex MKII), with the drift tube temperature set at 120° C. and the gas flow at 3.06 SLPM was used to detect all compounds present in the injection sample. The solvent system consisted of acetonitrile, water and aqueous 5% acetic acid as shown below:

| Time | Acetonitrile | Water |
| --- | --- | --- |
| 0 | 20 | 80 |
| 25 | 40 | 60 |
| 30 | 100 | 0 |
| 35 | 100 | 0 |
| 40 | 20 | 80 |

The flow rate was 1.0 mL/min.

Mass Spectrometry (MS)

Tandem liquid chromatography-mass spectrometry (HPLC-MS) analyses of pure compounds were performed using flow injection (FIA) with no column. The mobile phase consisted of methanol:water (70:30 v:v) and the flow rate was 1001 L/min. Solvents were delivered using a Hewlett Packard 1100 binary pump. Mass spectrometry analyses were conducted using a Micromass Quattro Spectrometer with an upgraded hexapole source operating in the electrospray positive mode. Scanning was done in the range of from 200 to 1500 m/z units with a cone voltage of 100 or 200 volts.

Figure 3A:
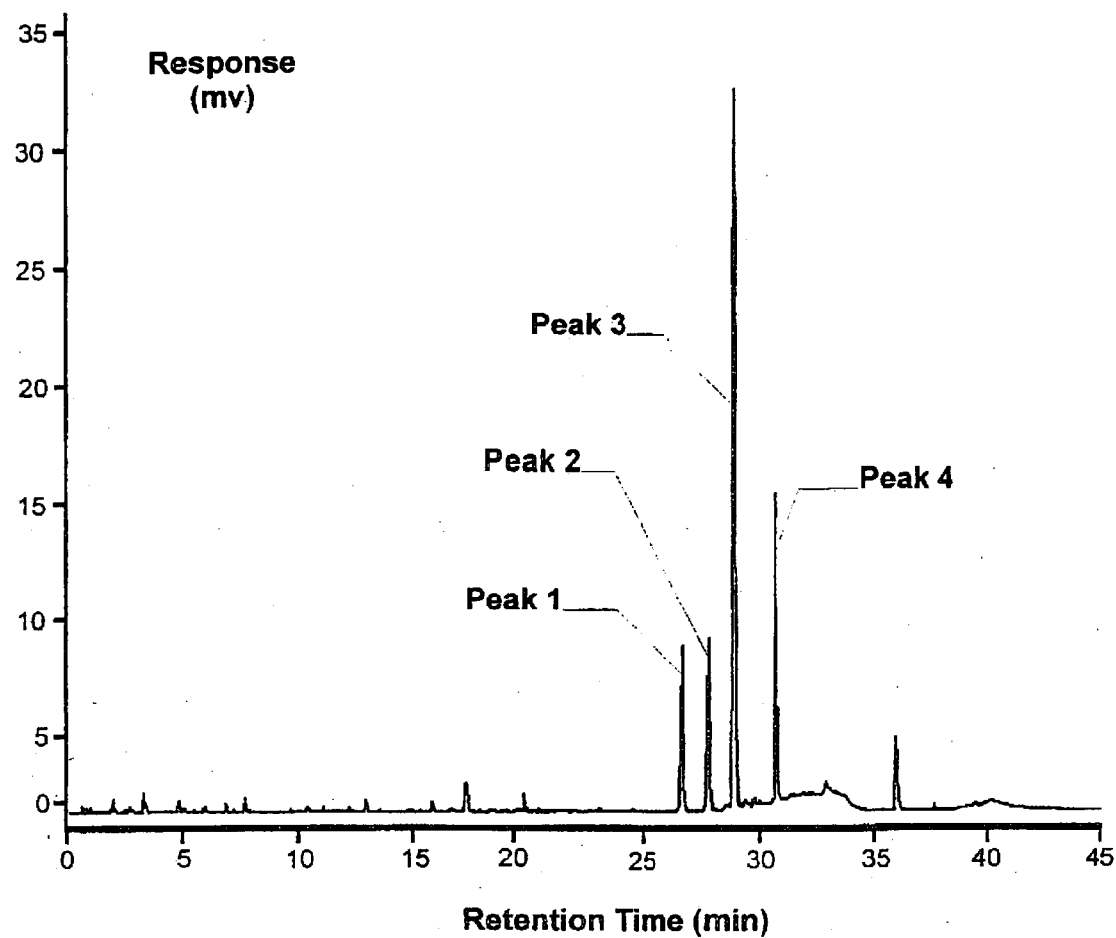
FIG. 3a shows the HPLC-ELSD profile of oat avenacin saponins and FIG. 3b shows the HPLC-ELSD profile of oat avenacoside saponins.
Figure 3B:
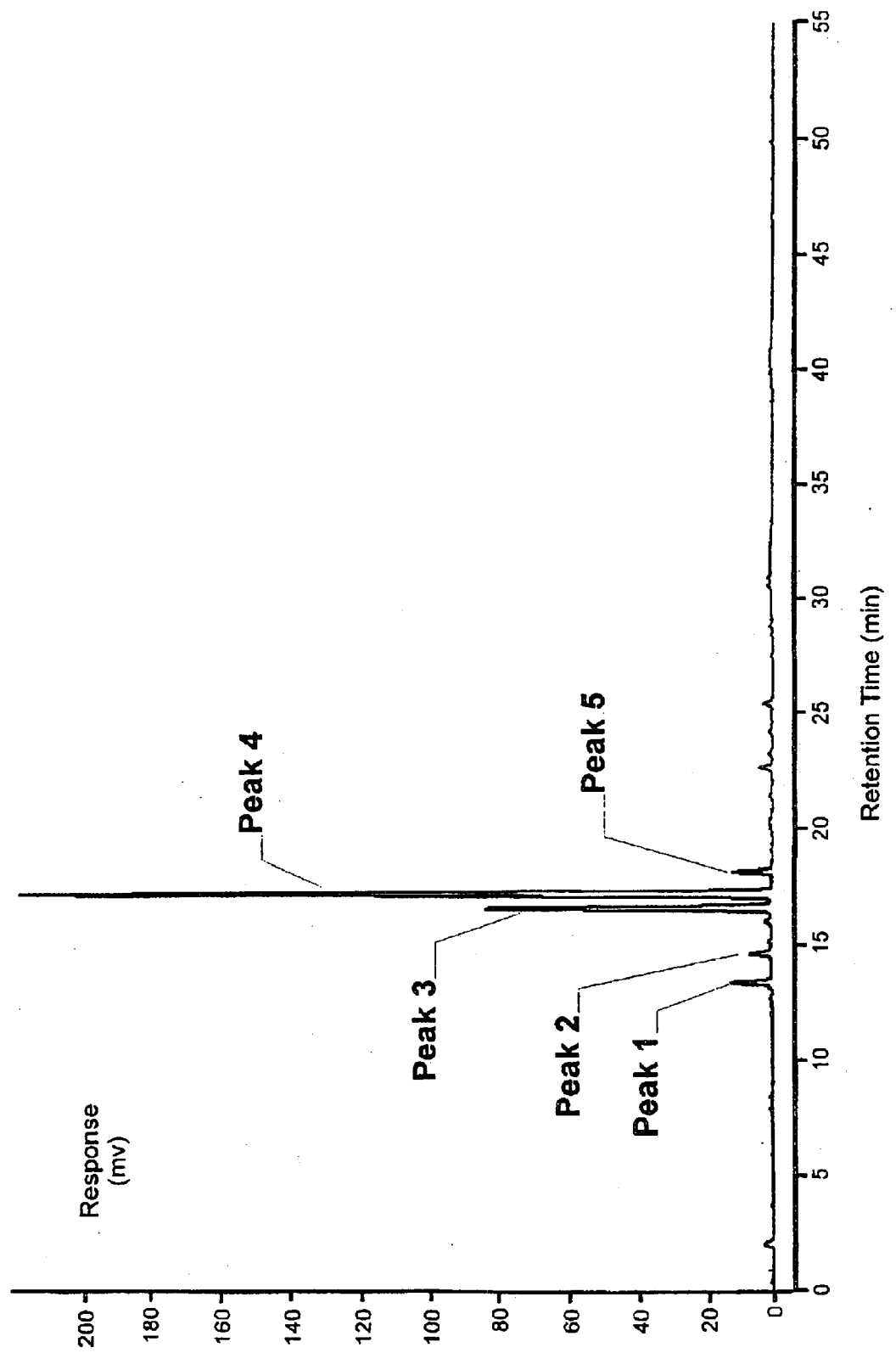

The "avenacin sub-fraction" prepared above was subjected to HPLC-ELSD analysis and a typical HPLC profile is shown in FIG. 3a. This sub-fraction corresponds to the 4 avenacins of Crombie et al. (Crombie, L., et al., J. Chem. Soc., Perk. Trans. 1, 1917–1922, 1986.). The "avenacoside sub-fraction" HPLC-ELSD profile (FIG. 3b), on the other hand, contained 5 peaks with 2 major peaks (Peaks 3 and 4). Of these, Peaks 3 and 4 had similar retention times to those reported for avenacosides B and A respectively, as reported by Kesselmeier and Strack (Kesselmeier, J. And Strack, D., Z. Naturforsch. 36C, 1072–1074, 1981).

It was found that individual components of both the avenacin-type saponins (i.e avenacins A-1, A-2 etc.) and the avenacoside-type saponins (i.e avenacosides A, B, C etc.) could also be separated by hydrophobic interaction chromatography by the judicious choice of both gel type and washing solvent composition. Thus, the avenacins-type saponins, which are relatively more non-polar than the avenacosides, were fractionated and purified on Octyl Sepharose CL-4B™ using isocratic washing with aqueous 25% and 30% ethanol. The avenacosides, containing more sugar residues than the avenacins, were fractionated and purified on SP Sephadex C-25™ in the HDTMA⁺ form, since these avenacosides were not completely retained on Octyl Sepharose CL-4B™, even with water as the solvent.

Figure 4A:
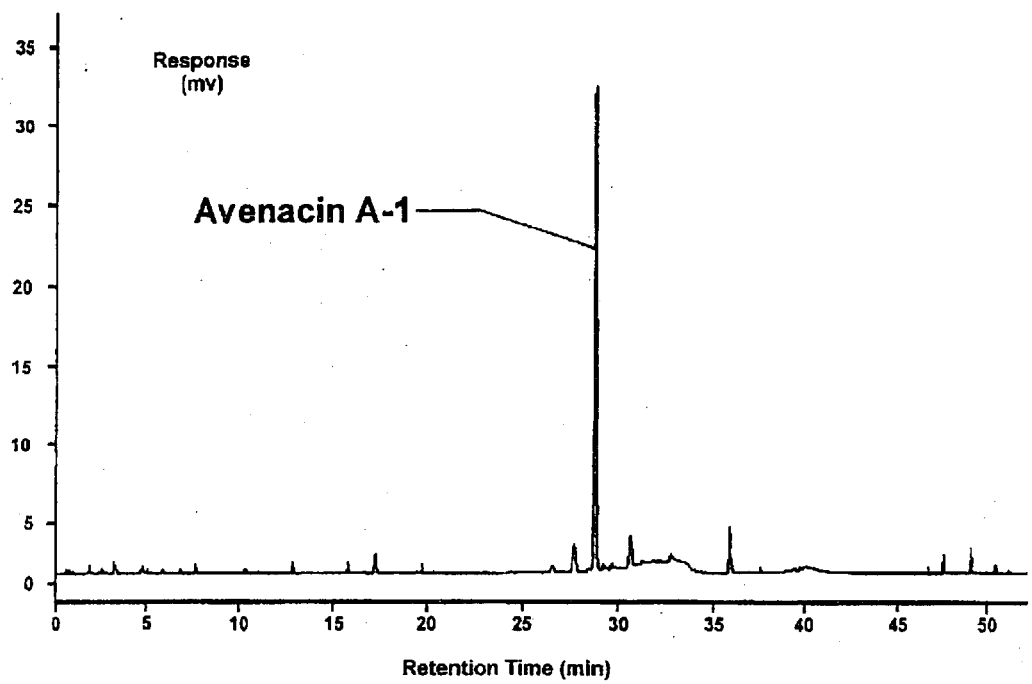
FIG. 4a shows the HPLC-ELSD profile of Octyl Sepharose CL-4B™ purified Avenacin A-1.
Figure 4B:
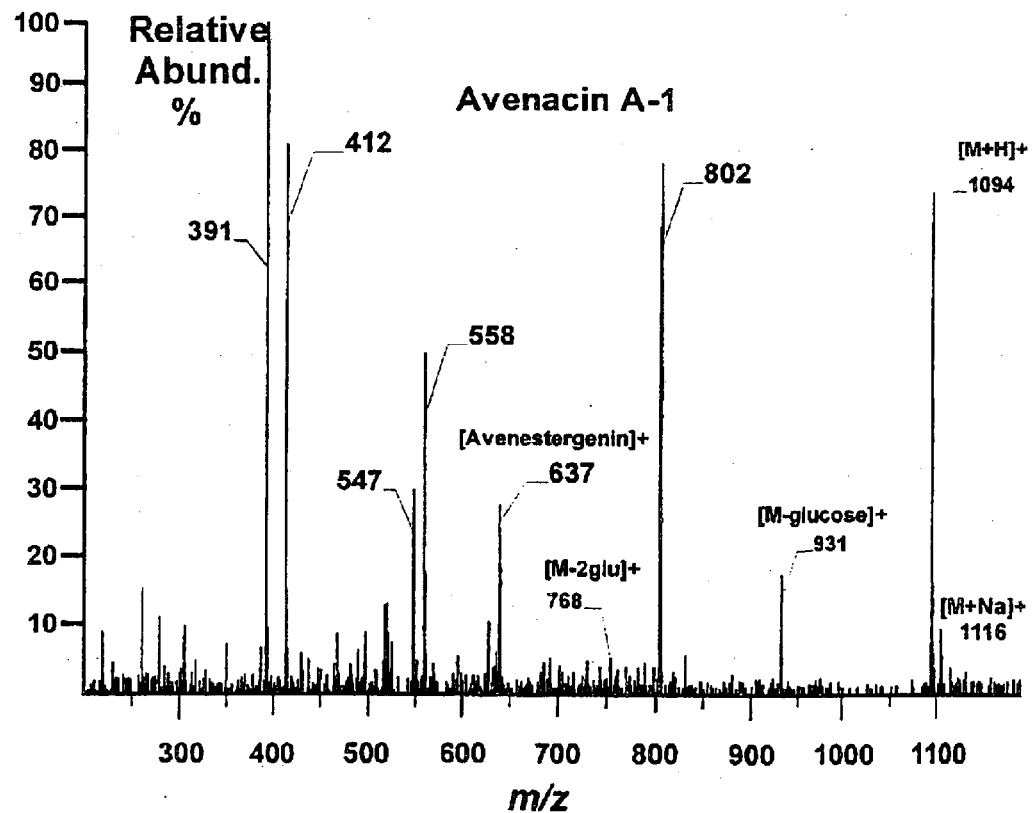
FIG. 4b shows the mass spectrum of purified Avenacin A-1.
Figure 4C:
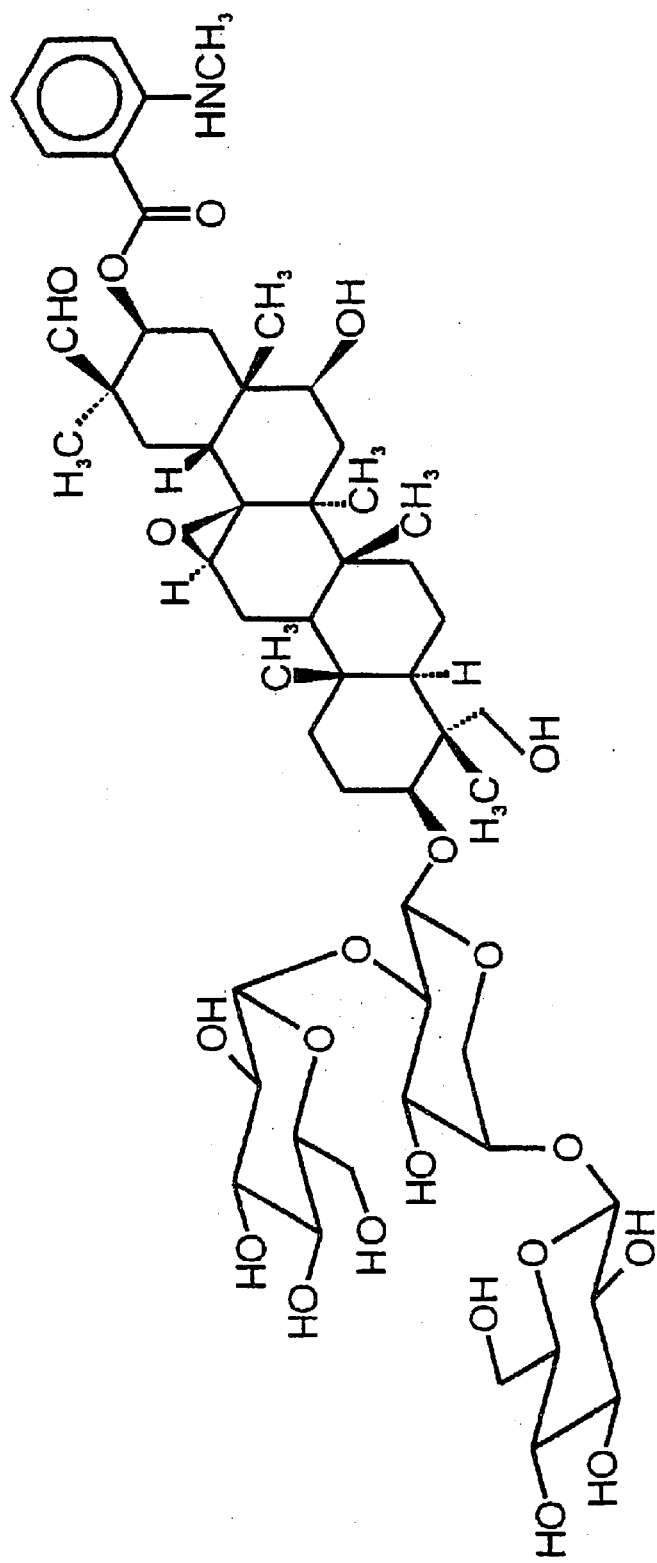
FIG. 4c shows the structure of Avenacin A-1 from oat groats.

For example, the "avenacin sub-fraction" prepared above was taken up in 10 mL aqueous 30% ethanol and absorbed onto a 30 mL (=$V_b$) graduated column of Octyl Sepharose CL-4B™ gravity packed and equilibrated in the same solvent. The column was then washed with the same solvent and fractions corresponding to the following K' values collected and analyzed for avenacins by TLC and HPLC. The fraction with K' from 2.5 to 5.5 contained all of the major avenacins observed in the HPLC profile (Peak 3, FIG. 3a) along with small amounts of minor avenacins and traces of avenacoside-like compounds. Further chromatography of this fraction on the same column but using aqueous 25% ethanol yielded the major avenacin peak in the fraction with K' from 6 to 8 at greater than 80% purity as determined by UV spectrophotometric (diode-array detection at 365 nm) and HPLC-ELSD analyses. Mass spectral analyses of this isolated peak confirmed its identity as avenacin A-1. FIG. 4a shows an HPLC-ELSD profile of the fraction obtained from the HIC column, while FIG. 4b shows the mass spectrum obtained from this peak, and the structure assigned to the avenacin is illustrated in FIG. 4c. Similarly, the remaining peaks can be individually purified simply by varying the amount of ethanol and water in the isocratic solvent to either increase or decrease the relative hydrophobic binding of the components in the mixture.

In a further example, the "avenacoside sub-fraction" prepared above was taken up in 10 mL aqueous 32.5% ethanol and absorbed onto a 30 mL (=$V_b$) graduated column of SP Sephadex C-25™ in the HDTMA$^+$ form, gravity packed and equilibrated in the same solvent. The column was then washed with the same solvent and fractions with K'<2.5, K' 2.5 to 5 and K'>5 collected and analyzed for avenacosides by TLC and HPLC. The fraction with K'<2.5 contained primarily avenacoside Peaks 2 and 3; K' 2.5 to 5 contained avenacoside Peaks 1 and 3 with small amounts of Peak 4, and the K'>5 fraction contained primarily avenacoside Peaks 4 and 5 with a small amount of Peak 3.

Example 2

Isolation of Saponins from Quinoa Flour Using Hydrophobic Interaction Chromatography on Octyl Sepharose CL-4B™ and Novel Substituted Hydrophobic Gels In the following example the quinoa saponins were isolated and highly purified as an entire group using HIC. Advantage was also taken of the fact that none of the saponins carries a cationic charge within the working range of the invention, and thus passage of the extracted mixture through a cation exchange column will not remove any of the saponins from the mixture. A final saponin-enriched fraction substantially free of interfering compounds of like solubility was prepared using only ethanol, water, and volatile acids and bases.

Thin Layer Chromatography (TLC)

TLC was performed as described in Example 1.

High Performance Liquid Chromatography (HPLC)

HPLC analyses were conducted using the same equipment as described in Example 1 except a $C_8$ Keystone column 120 Å, 5 μm, (250×4.6 mm) was used and a UV diode array detector (Thermo Separation Products, Spectra-SYSTEM UV 3000), monitoring at 270 nm (general phenolic functional group absorption) was linked in tandem with the ELSD detector operated as in Example 1. This allowed simultaneous detection of non-saponin phenolic components. The solvent system consisted of acetonitrile, $H_2O$, and aqueous 5% glacial acetic acid (v %):

| Time | Acetonitrile | $H_2O$ | 5% Acetic acid |
|---|---|---|---|
| 0 | 15 | 75 | 10 |
| 25 | 25 | 65 | 10 |
| 29 | 100 | 0 | 0 |
| 33 | 100 | 0 | 0 |
| 35 | 15 | 75 | 10 |

The flow rate was 1.0 mL/min.

Thus, quinoa seeds (Cultivar Colorado 407 (CO07)) were ground to pass 20 mesh to produce a flour. To a heated solution (60° C.) of 100 mL of acidified aqueous 80% ethanol (ethanol:water:glacial acetic acid 80:19:1, v:v:v), 25 g of the flour was carefully added with stirring (solids/liquids=1/4 v:v). The mixture was allowed to stir for 30 minutes and then cooled to room temperature. The mixture was centrifuged (2830×g, 7 minutes) and the supernatant drawn off. The pellet was washed with fresh solvent (200 ml) and re-centrifuged. The supernatant was drawn off and the pellet re-suspended a third time with fresh solvent. All supernatants were combined and filtered through a course sintered glass filter. The dark yellow filtrate, constituting an extract, had a pH of 7.03 and contained 7.3% solubles as determined by gravimetric analysis of a freeze-dried sub-sample.

The extract was evaporated to dryness in vacuo by rotary evaporation at 40° C. and taken up in 2.5 ml of acidified aqueous 50% ethanol (ethanol:water:glacial acetic acid 50:49:1, v:v:v). The cloudy suspension was loaded onto a graduated glass column of Octyl Sepharose CL-4B™ column (final packed $V_b$=25 mL; i.e. 1 mL gel/gm quinoa flour extracted) pre-equilibrated and gravity packed in acidified aqueous 40% ethanol (ethanol:water:glacial acetic acid 40:59:1, v:v:v). The column was then washed with 2×$V_b$ of the acidified aqueous 50% ethanol to give a K'≦2 fraction which was concentrated in vacuo at 40° C. by rotary evaporation to a yellow syrup. TLC analyses of this fraction (K'≦2) showed it contained the quinoa saponins, sugars, amino acids, organic acids, and some of the pigments amongst others. The material remaining on the column was removed (and the column regenerated for re-use), by passing 2×$V_b$ of acidified aqueous 80% ethanol to give a K'≧2 fraction. TLC of this fraction showed it contained the bulk of the polar lipids and some of the pigments but no traces of saponin. Gravimetric analyses showed that this K'≧2 fraction constituted about 1.2% of the original quinoa flour while the saponin-enriched K'≦2 fraction represented over 6.4% of the flour.

The K'≦2 fraction prepared above was taken up in 50 mL of aqueous 50% ethanol and applied to a graduated glass column of SP Sephadex C-25™ in the ammonium form (final packed $V_b$=25 mL; i.e. 1 mL gel/gm quinoa extracted), pre-equilibrated and gravity packed in aqueous 50% ethanol. The column was then washed with 2×$V_b$ of the aqueous 50% ethanol to give a K'≦2 fraction, containing the neutral and anionic components, which was concentrated in vacuo at 40° C. by rotary evaporation to a pale yellow syrup. The cationic material on the column was then recovered by passing 2×$V_b$ of 5% ammoniacal aqueous 50% ethanol (i.e. ethanol:water:conc. ammonium hydroxide 50:45:5 v:v:v) and by concentrating this K'≧2 fraction in vacuo at 40° C. by rotary evaporation to remove the solvent and excess ammonia. By gravimetric analyses, this cationic fraction was found to represent about 1% of the quinoa flour while the K'≦2 fraction constituted more than 5.3%. TLC analyses of these fractions showed that all the saponins were present in the K'≦2 fraction along with the sugars, organic acids, and some of the amino acids, protein and pigments amongst others, while the K'≧2 fraction showed no traces of saponins.

Figure 5:
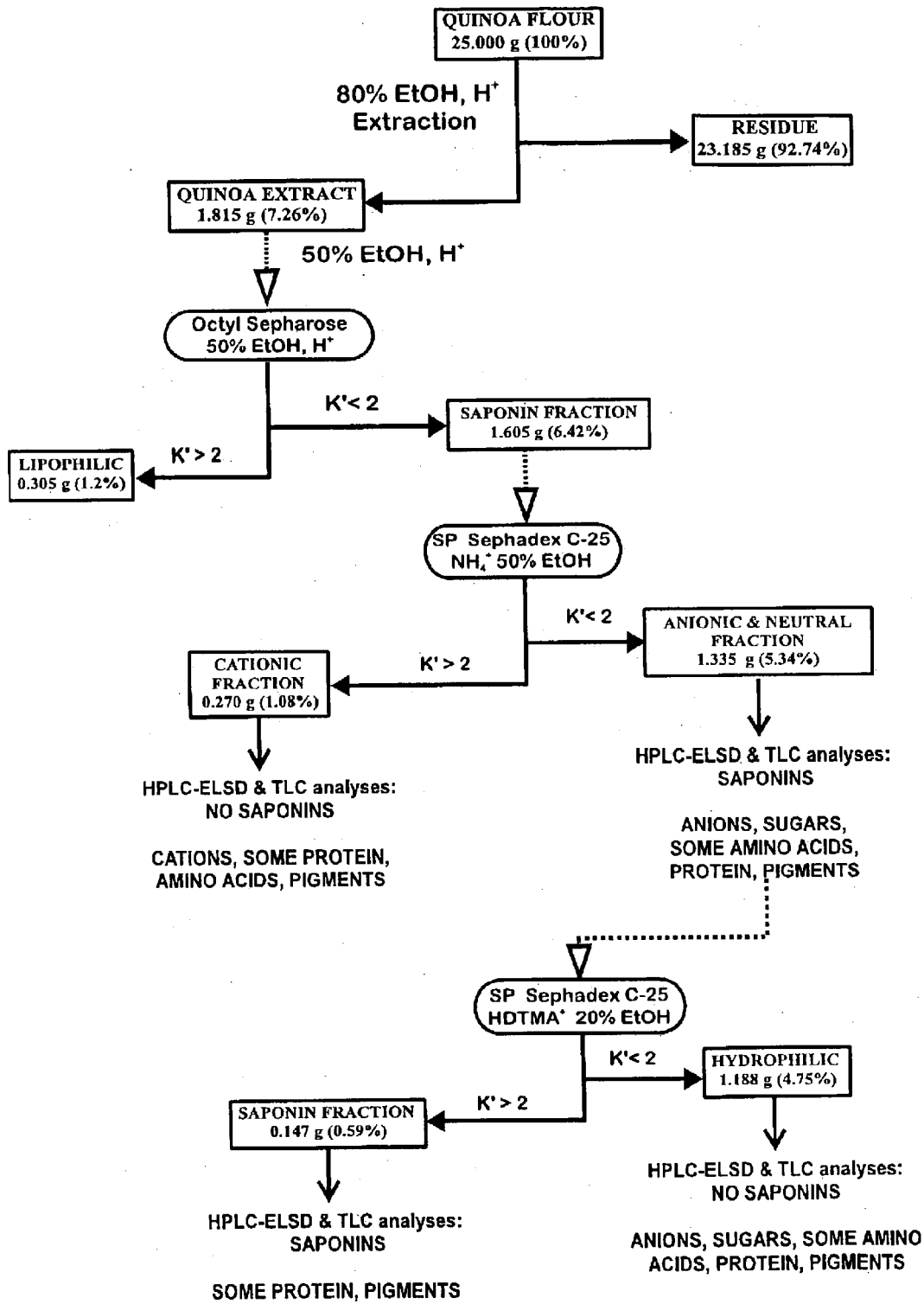
FIG. 5 shows the isolation and group separation of saponins from quinoa.

Further purification of the saponins was carried out using HIC on a 25 mL graduated glass column of SP Sephadex C-25™ in the HDTMA$^+$ form, prepared as in Example 1 (final packed $V_b$=25 mL; i.e. 1 mL gel/gm quinoa extracted), pre-equilibrated and gravity packed in aqueous 20% ethanol. The anionic and neutral K'≦2 fraction prepared above was taken up in 2.5 mL aqueous 20% ethanol, loaded onto the column and washed with 2×$V_b$ of the 20% aqueous ethanol to give a K'≦2 fraction. The material still absorbed on the column was then recovered by passing 2×$V_b$ of aqueous 80% ethanol through the column to give an enriched saponin fraction. Both fractions were then evaporated to dryness in vacuo at 40° C. by rotary evaporation and analyzed by gravimetric analysis, TLC and HPLC. The K'≦2 fraction representing about 4.75% of the original quinoa flour was devoid of saponins while the K'≧2 fraction constituting about 0.59%, showed a highly enriched saponin content by both HPLC and TLC. The scheme for the isolation and group separation of quinoa saponins is summarized in FIG. 5.

HPLC-ELSD with simultaneous HPLC-UV analyses of this enriched quinoa saponin fraction showed that the fraction w as substantially free of maj or interfering non-saponin components. The HPLC-ELSD profile showed 3 major peaks at retention times of between 21 and 29 minutes. When compared on the same scale of response, the HPLC-UV profile showed several minor non-saponin peaks containing phenolic functions absorbing at 270 nm, eluting between 4 and 8 minutes, that were also present in the ELSD profile. TLC analysis showed these non-saponin components to include phenolic pigments, some amino acids, and some protein-like material, amongst others. Fractional integration of all the ELSD peaks enabled the approximate purity of this enriched saponin fraction to be estimated at greater than 90%.

Figure 6A:
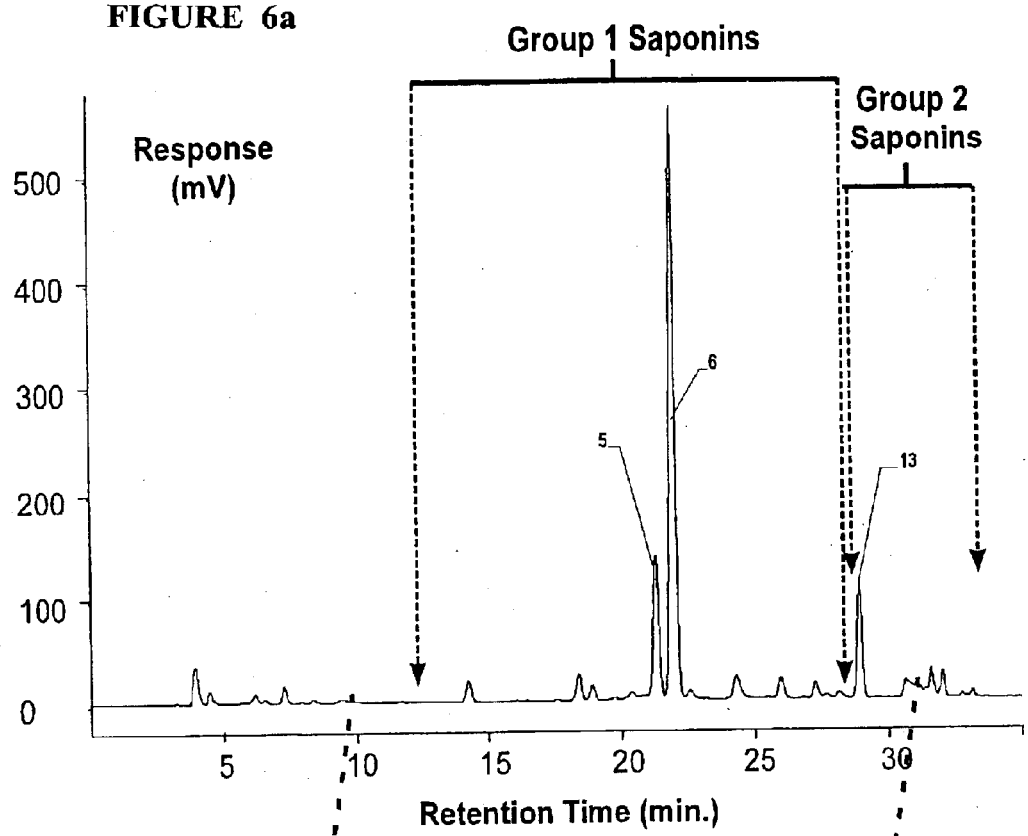
FIG. 6a and FIG. 6b show the HPLC-ELSD assignments for the quinoa saponins.
Figure 6B:
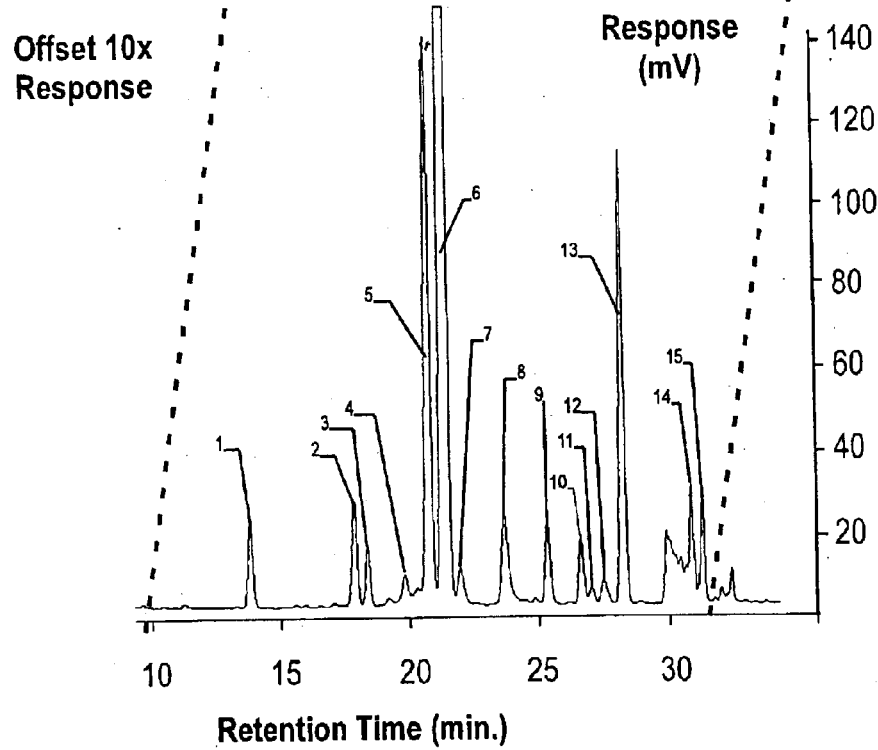

Considering the elution gradient used in the HPLC analysis, the quinoa saponins can be roughly divided into two major groups, as shown in FIGS. 6a and 6b, based on relative hydrophobicity. The relatively less hydrophobic quinoa Group 1 saponins eluted from between 14 and 27 minutes during that portion of the gradient utilizing from 15% to 25% acetonitrile in the solvent. This group consisted of at least 12 chromatographically distinct saponins with peaks 5 and 6 const tuling the major components. Quinoa Group 2 saponins on the other hand eluted only after rapid ramping of the elution gradient to 100% acetonitrile and contained one major component, peak 13, and at least 2 additional saponins, bringing the total to at least 15 saponins from the particular cultivar.

As a further example of the chromatographic purification applications of the present invention, the quinoa saponins were subjected to additional fractionation into Group 1 saponins and Group 2 saponins, and the remaining non-saponin components simultaneously removed. In this application, use was made of the differences between the two saponin groups and their relative hydrophobic binding to a novel substituted hydrophobic gel. Some of the non-saponin components were first removed by anionic exchange chromatography.

Thus, the enriched saponin fraction prepared above (i.e. K'≧2 in 20% ethanol on SP Sephadex C-25™ in the HDTMA⁺form) was evaporated to dryness under reduced pressure and taken up in aqueous 50% ethanol (5 ml). The yellowish solution was applied to a 25 mL anion exchange column of QAE Sephadex A-25™ prepared essentially as described in Example 1 except converted to the formate form in stead of the acetate form, and pre-equilibrated in aqueous 50% ethanol (final packed volume $V_b$=25 ml; i.e. 1 ml gel/gm quinoa flour extracted). The column was then washed with $2×V_b$ of aqueous 50% ethanol to give a K'≦2 fraction which was evaporated to dryness in vacuo at 40° C. by rotary evaporation. The material still absorbed onto the column was then removed by passing $3×V_b$ of acidified aqueous 50% ethanol (ethanol:water:formic acetic acid 50:45:5 v:v:v) through the column to produce a K'≧2 faction which was also evaporated to dryness in vacuo at 40° C. by rotary evaporation. Both fractions were then analyzed by TLC and HPLC. As shown in the reproduction of the TLC plate of the K'≦2 fraction (FIG. 7a), this fraction contained all of the saponins along with the yellow pigments. No saponins were detected in the K'≧2 fraction.

Figure 8:
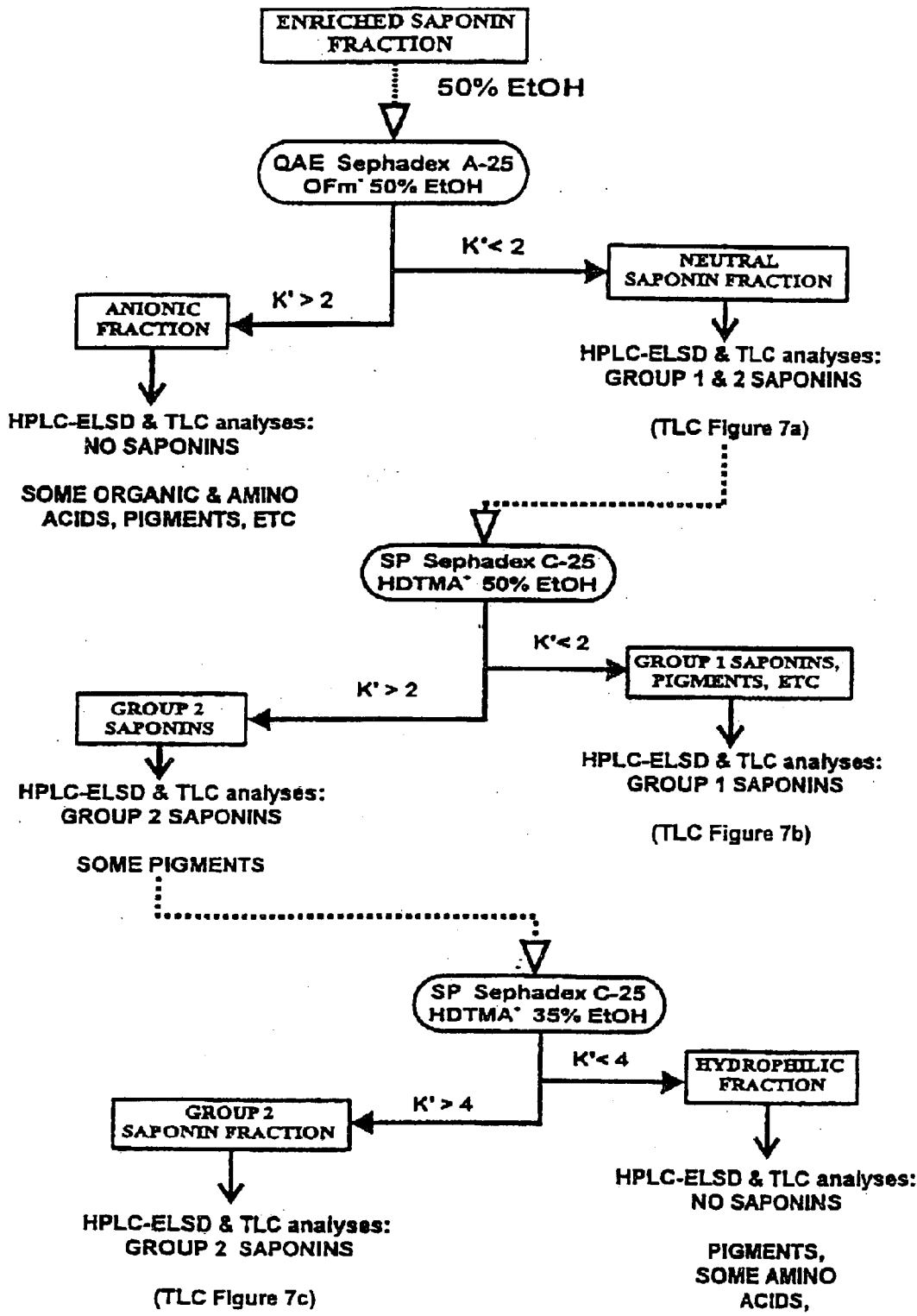
FIG. 8 shows the purification and separation of quinoa Group 1 and 2 saponins.

The next step was to separate the quinoa Group 1 saponins from Group 2 saponins by HIC on SP Sephadex C-25™ in the HDTMA⁺ form. Thus the K'≦2 fraction from the previous anion exchange step was taken up in 2.5 mL of aqueous 50% ethanol and absorbed onto a graduated glass column of SP Sephadex C-25™ in the HDTMA⁺ form, prepared and gravity packed as previously described and pre-equilibrated in aqueous 50% ethanol (final packed volume $V_b$=25 ml; i.e. 1 mL gel/gm quinoa flour extracted). The column was then washed with $2×V_b$ of aqueous 50% ethanol to give a K'≦2 fraction. The material still absorbed on the column was then removed by passing $2×V_b$ of aqueous 80% ethanol through the column to produce a K'≧2 fraction. Both fractions were then evaporated to dryness in vacuo at 40° C. by rotary evaporation and analyzed by TLC and HPLC. As shown in the reproduction of the TLC plate of the K'≦2 fraction (FIG. 7b), this fraction contained essentially only the Group 1 quinoa saponins as determined by HPLC-ELSD analysis and was devoid of pigments. By comparison of HPLC-ELSD fractional integration and the TLC spot intensities, the major zone on the TLC plate with $R_f$ values between 0.19 and 0.26 (FIG. 7b) corresponded to peak 13. Fractional integration of all the ELSD peaks enabled the approximate purity of this saponin fraction to be estimated at greater than 99%. The K'≧2 fraction contained the rest of the saponins and the phenolic pigments which could be separated by a final treatment with the same HIC gel but using a solvent with a higher water content. Thus, the K'≧2 fraction containing the Group 2 saponins and the pigments was taken up in 2.5 mL of aqueous 35% ethanol and absorbed onto the same column of SP Sephadex C-25™ in the HDTMA⁺form, pre-equilibrated in aqueous 35% ethanol (final packed volume $V_b$=25 ml; i.e. 1 mL gel/gm quinoa flour extracted). The column was washed with $4×V_b$ of aqueous 35% ethanol to give a K'≦4 fraction which was evaporated to dryness in vacuo at 40° C. by rotary evaporation to give a yellowish lacquer. The material still absorbed on the column was then removed by passing $2×V_b$ of aqueous 60% ethanol through the column to produce a K'≧4 fraction. Rotary evaporation of this fraction to dryness in vacuo at 40° C. gave a white powder. TLC and HPLC-ELSD analyses of the K'≦4 revealed no saponins in this fraction but most if not all of the pigments. On the other hand, as shown in the reproduction of the TLC plate of the K'≧4 fraction (FIG. 7c), this fraction contained essentially only the Group 2 quinoa saponins as determined by HPLC-ELSD analysis and was devoid of pigments. The major peaks 5 and 6 appeared as close running zones on the TLC plate with $R_f$ values between 0.40 and 0.48. Fractional integration of all the ELSD peaks enabled the approximate purity of this saponin fraction to be estimated at greater than 99%. The scheme for the purification and separation of quinoa Group 1 and 2 saponins is summarized in FIG. 8.

Example 3

Comparative Utility of Ionically-Substituted vs. Covalently-Substituted Gels for the Separation and Purification of Saponins using Hydrophobic Interaction Chromatography Macroporous chromatographic media, based on a polysaccharide backbone and containing any one of a number of different covalently-linked alkyl ligands with chain lengths up to 12 carbons, are commercially available. Examples of such products include for example Butyl Sepharose™ Amersham Pharmacia Biotech, Piscataway, N.J.), aminohexyl agarose($C_6$) and dodecyl agarose($C_{12}$) (Sigma Chemical Co., St. Louis, Mo.). These gels, for the most part suffer from low ligand substitution rates, typically ≦40 µM ligand/mL gel, resulting in relatively low hydrophobic interaction capacity for low molecular weight compounds, and high costs. According to the present invention, hydrophobic interaction chromatographic separations can be effectively and efficiently carried out on macroporous, highly substituted anionically- or cationically-charged polysaccharide gels using any one of a wide variety of hydrophobic counterions. Such gels are easily and reversibly generated at the time of use and are stable under most physiological and biochemical working conditions.

The practice of reverse phase and hydrophobic interaction chromatography teaches that, in general, under identical elution conditions the relative binding affinity of a specific substrate to a hydrophobic ligand substituted on the stationary phase will increase with increasing chain length of the ligand. To show the utility of these readily-modified gels and to compare their relative binding properties, a series of experiments was performed using identical column and substrate conditions but varying the type of stationary phase gel ligand chain length and the recovery solvent composition (i.e. aqueous ethanol). The gel matrices were as follows: Butyl Sepharose™ and Octyl Sepharose CL-4B™ as received from the manufacturer; QAE Sephadex A-25™ in the dodecyl sulfate form, prepared as described below, and SP Sephadex C-25™ in the hexadecyltrimethylammonium form, prepared as described below. It should be pointed out that none of these gel matrices show any appreciable absorption or fluorescence in long wave UV light (365 nm). The substrate was the saponin avenacin A-1, prepared and purified from oat groats as described in Example 1. This saponin contains an N-methylanthraniloyl moiety which is strongly autofluorescent in solution at 365 nm permitting on-column monitoring of its migration through the gel matrix simply by observing the graduated glass column under long wave UV light. Column beds were 30 mL gravity-packed in a volumetrically-graduated glass column fitted with a medium-porosity polypropylene fritted disk.

Basically, either of the two different types of ion exchangers, anionic or cationic, preferably consisting of an ionically-substituted polysaccharide gel, can be used as the hydrophilic core. To this core a hydrophobic ligand, containing a strongly ionizable functional group of opposite charge to that of the polysaccharide, is attached by ion exchange so that all, or substantially all, of the available ionic sites in the original polysaccharide are occupied by the ligand to form a modified, hydrophobic phase component. Thus, in this example QAE Sephadex A-25™ anion exchange chromatography gel, in the chloride form (as received from the manufacturer), containing 0.5 milliequivalents/mL exchange capacity (Amersham Pharmacia Biotech, Piscataway, N.J.) was swollen and equilibrated in aqueous 50% ethanol and gravity packed into a volumetrically-calibrated chromatography column to give a bed of known volume. The column was first converted to the hydroxide form by passing excess 0.5N NaOH in 50% ethanol through the column and washing the bed to neutral pH with aqueous 50% ethanol. The bed was then converted to the lauryl sulfate form by passing a 2-fold milliequivalent excess of sodium dodecyl sulfate in aqueous 50% ethanol (SDS, Fisher Scientific, Ottawa, ON) and again washing the column with aqueous 50% ethanol to remove any excess SDS. By using a strongly ionized (e.g. sulfate) anionic detergent containing a linear aliphatic component of 12-carbons the chromatographic media has been substantially modified to give a HIC column which is relatively stable over the pH range 2.5–11 and has increased capacity for hydrophobic interaction due to the longer alkyl chain length, than readily available gels (C-12 vs. C-8 for Octyl-Sepharose CL-4B™), and about 10 times greater degree of substitution (for example, nominally 0.5 millimoles/mL vs. 50 µmoles/mL for Octyl-Sepharose CL-4B™), while still maintaining attributes suitable for HIC applications.

Similarly, a modified chromatography media suitable for HIC was prepared using an analogous process and a cationic ion exchanger. Thus, for example, SP Sephadex C-25™ cation exchange chromatography gel, in the sodium form (as received from the manufacturer), containing 0.3 milliequivalents/mL exchange capacity (Amersham Pharmacia Biotech, Piscataway, N.J.) was swollen and equilibrated in aqueous 50% ethanol and gravity packed into a volumetrically-calibrated chromatography column to give a bed of known volume. The column was first converted to the hydronium form by passing an excess of 0.1N HCl in aqueous 50% ethanol through the column and washing the bed to neutral pH with aqueous 50% ethanol. The bed was then converted to the hexadecyltrimethylammonium form by passing a 2-fold milliequivalent excess of hexadecyltrimethylammonium bromide in aqueous 50% ethanol (HDTMA, Sigma Chemical Co., St. Louis, Mo.) and washing the column with aqueous 50% ethanol to remove any excess HDTMA. Again, by using a strongly ionized (e.g. quaternary amine) cationic detergent containing a linear aliphatic component of 16-carbons the chromatographic media has been substantially modified to give a HIC column, which is relatively stable over the pH range 2.0–13, and has increased capacity for hydrophobic interaction due to the longer alkyl chain length, than readily available gels (C-16 vs. C-8 for Octyl Sepharose CL-4B™), and almost 10 times greater degree of substitution (for example, nominally 0.3 millimoles/mL vs. 50 µmoles/mL for Octyl Sepharose CL-4B™), while still maintaining attributes suitable for HIC applications.

The degree of relative hydrophobic interaction of the substrate was obtained from K' values, as previously defined by direct measurement of the on-column fluorescent band. K' values were recorded for both the leading and tailing edge of the fluorescent zone and these K' values averaged. The results are summarized in Table 1 using SP Sephadex C-25™ columns in the alkyl trimethylammonium form substituted with different chain lengths.

TABLE 1

Effect of Hydrophobic Ligand Chain Length on Binding of Avenacin A-1

| Washing Solvent (EtOH:H$_2$O) | Average K' Value with Different Ligand Side Chains | | | | | |
|---|---|---|---|---|---|---|
| (v:v) | C$_4$ | C$_8$ | C$_{12}$ | C$_{14}$ | C$_{16}$ | C$_{18}$ |
| 10:90 | 12.75 | 19.5 | | | | |
| 20:80 | 5.66 | 11.75 | | | | |
| 30:70 | 1.74 | 3.99 | | | | |
| 40:60 | 1.24 | 1.45 | 4.83 | 5.25 | 7.56 | 9.82 |
| 50:50 | | 1.19 | 1.63 | 1.68 | 1.92 | 2.44 |
| 60:40 | | | 1.08 | 1.18 | 1.26 | 1.55 |

Figure 9:
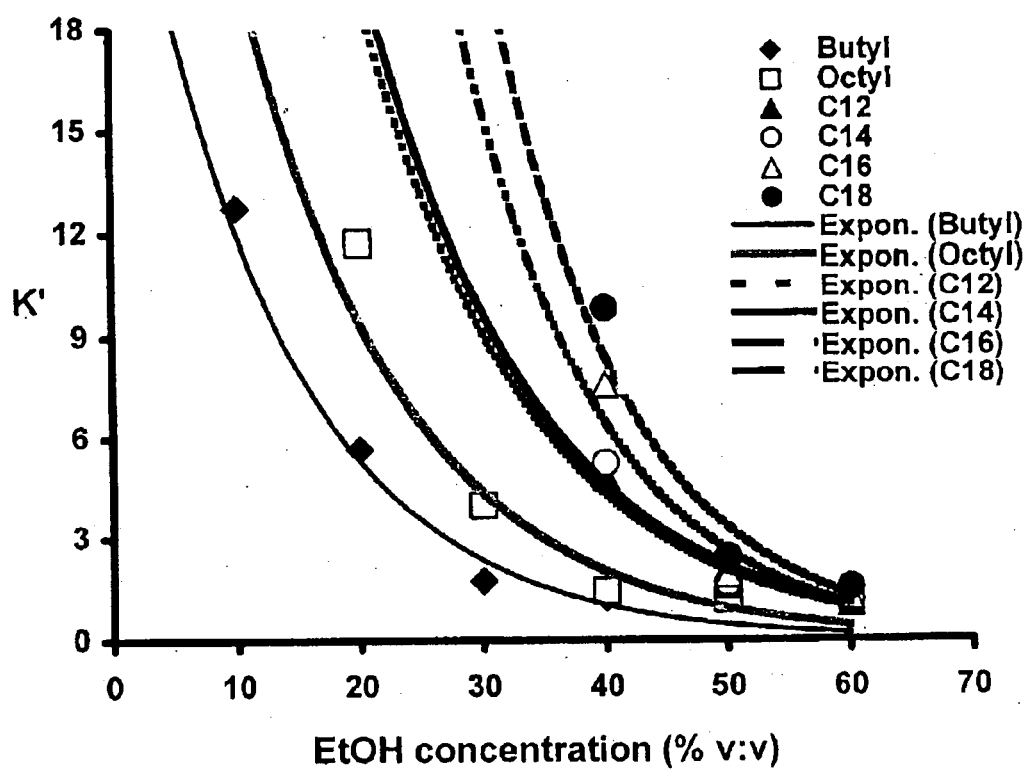
FIG. 9 shows the relationship between ethanol concentration and chain length for various K' values of Avenacin A-1 on SP Sephadex C-25™ alkyl trimethylammonium columns with different chain lengths.
Figure 10:
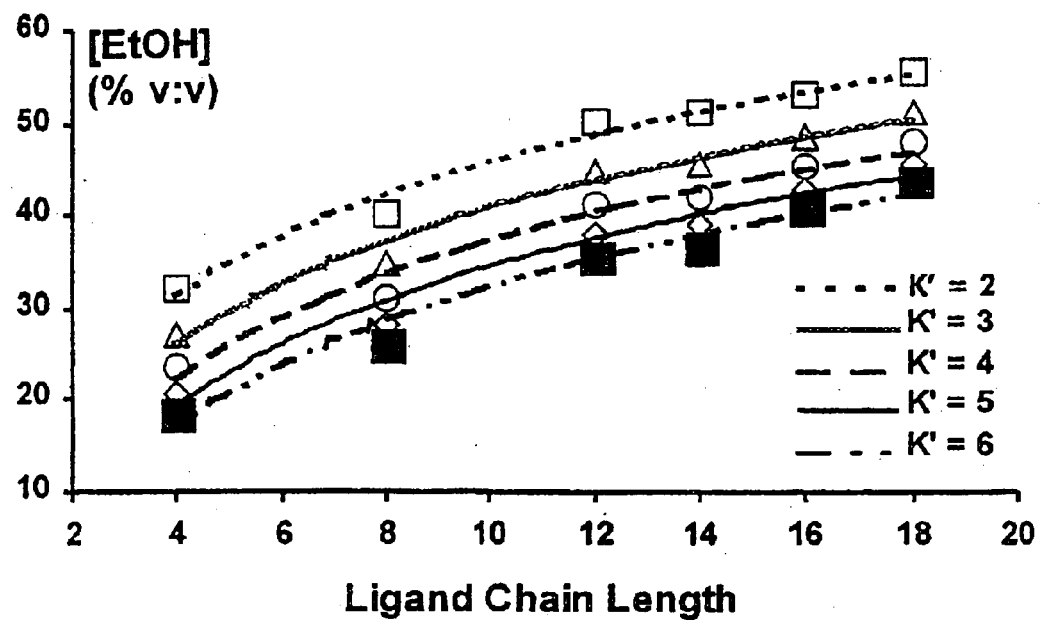
FIG. 10 shows the relationship between ethanol concentration on K' values as in FIG. 9, only expressed in terms of chain length.

These results are depicted in FIGS. 9 and 10. In FIG. 9 the effect of ethanol concentration on K' values of avenacin A-1 using different chain length substitutions is shown. According to the present invention, separation will be most effective in the steep slope of the graph. In this area of the graph a small change in ethanol concentration results in a large change in K' value, thus allowing effective separation between two compounds so that they can be isolated from each other. On the other hand, at the end of the graph, where the slopes of the curves converge, two compounds will elute from the column together, as changing the ethanol concentration does not result in a large change in K' values. FIG. 10 is a plot of the same results showing the effect of ethanol concentration and substrate hydrophobicity on K' values for avenacin A-1, as a function of the chain length. Thus these graphs can be used to assist in choosing the optimum ethanol concentration and column chain length for separations of compounds from, in this example, avenacin A-1. As will be clear to persons of ordinary skill in the art, similar series of experiments can be conducted on other compounds of interest to be isolated, in order to deduce an appropriate purification strategy.

Table 2 shows a comparison between the use of a QAE-Sephadex A-25™ dodecyl sulfate column and a SP Sephadex C-25™ dodecyltrimethylammonium column. Although there are differences in the K' values between the two columns, the relationship between K' value and the concentration of ethanol is the same.

TABLE 2

Effect Column Types on Binding of Avenacin A-1

| Washing Solvent (EtOH:H$_2$O) (v:v) | Average K' Value | |
|---|---|---|
| | QAE Sephadex A-25 ™ Dodecyl sulphate (C12) | SP Sephadex C-25 ™ Dodecyl-trimethylammonium (C12) |
| 10:90 | | |
| 20:80 | | |
| 30:70 | | |
| 40:60 | 3.33 | 4.83 |
| 50:50 | 0.70 | 1.63 |
| 60:40 | 0.53 | 1.08 |

All scientific publications and patent documents are incorporated herein by reference.

The present invention has been described with regard to preferred embodiments. However, it will be understood to persons skilled in the art that a number of variations and modifications can be made without departing from the scope of the invention as described in the following claims.

What is claimed is:

1. A method of isolating a non-polar extractive comprising:
   contacting said non-polar extractive in an aqueous organic solution with a gel matrix selected from the group of an electrostatically-linked, aliphatic or alicyclic-substituted anionic or cationic polysaccharide gel;
   washing said gel matrix with said aqueous organic solvent solution;
   washing said gel matrix with additional aqueous organic solvent solution,
   wherein the proportion of the organic solvent in said solution is increased; and
   recovering said extractive from an effluent stream.

2. The method of claim 1, further comprising regenerating the gel matrix for re-use.

3. The method according to claim 1, wherein the non-polar plant extractives are selected from the group consisting of steroids and triterpenoids, flavonoids, phenolic conjugates, polar lipids, and prolamines.

4. The method according to claim 3, wherein the steroids and triterpenoids are selected from die group consisting of saponins, cardiac glycosides and steryl conjugates.

5. The method according to claim 3, wherein the flavonoids are selected from the group consisting of flavones, flavonols, isoflavones and all of their glycosides.

6. The method according to claim 3, wherein the phenolic conjugates are selected from the group consisting of aliphatic alcohol esters and amides.

7. The method according to claim 3, wherein the polar lipids are selected from the group consisting of mono- and di-glycerides and their derivates and alk(en)yl resorcinols.

8. The method according to claim 3, wherein the prolamines are selected from the group consisting of zein, avenin, hordein and gliadin.

9. The method according to claim 3, wherein the non-polar extractives are from either synthetic or natural source.

10. The method according to claim 9, wherein the natural source of the non-polar extractives is selected from the group consisting of plant material, algae, fungi and unicellular organisms.

11. The method according to claim 10, wherein the plant material is selected from the group consisting of agricultural, viniculture, horticulture, aquaculture and plants native to lands and oceans.

12. The method according to claim 11, wherein the agricultural plant material is selected from the group consisting of wheat, oats, rye, corn, rice, quinoa, amaranth, buckwheat, triticale or barley; or oilseeds, such as soybean, canola, flaxseed, sunflower, safflower or mustard; or pulsecrops, for example, peas, lentils or beans; or forage crops, such as fescue, timothy, clover, alfalfa or wheatgrass; or herbs, such as parsley, rosemary, sage, or mint.

13. The method according to claim 1, wherein the organic solvent solution is a solution containing a lower alcohol, a ketone or a combination thereof.

14. The method according to claim 13, wherein the lower alcohol is selected from the group consisting of methanol, ethanol, propanol and isopropanol.

15. The method according to claim 13, wherein the ketone is acetone.

16. The method according to claim 1, wherein the cationic polysaccharide gel is a neutral polysaccharide of the any-hydrogalactan or dextran class containing covalently-linked cationically-charged functional groups.

17. The method according to claim 16, wherein the cationically-charged functional groups are selected from the group consisting of tertiary amines and quaternary amines.

18. The method according to claim 1, wherein the cationic polysaccharide gel is selected from the group consisting of diethyaminoethyl polydextran, quaternary aminoethyl polydextran, and quaternary amine crosslinked agarose.

19. The method according to claim 1, wherein the anionic polysaccharide gel is a neutral polysaccharide of the any-hydrogalactan or dextran class containing covalently-linked anionically-charged functional groups.

20. The method according to claim 19, wherein the anionically-charged functional groups are selected from the group consisting of alk(en)yl sulfonates and alk(en)yl phosphonates.

21. The method according to claim 1, wherein the anionic polysaccharide gel is selected from the group consisting of sulphonate crosslinked agarose.

22. The method according to claim 1, wherein the hydrophobic ligand is an anionic detergent selected from the group consisting of alk(en)yl sulfonates and sulfates, alk(en)ylbenzenesulfonates, taurocholates and taurodeoxycholates, alk(en)yl phosphonates and phosphates, and mono- and di-alk(en)ylphosphatidic acids.

23. The method according to claim 22, wherein the alk(en)yl substitution contains from about 4 to about 18 carbons.

24. The method according to claim 22, wherein the anionic detergent is sodium dodecyl sulfate.

25. The method according to claim 1, wherein the hydrophobic ligand is a cationic detergent selected from the group consisting of alk(en)yltrimethylammonium halides and quaternary alk(en)ylammonium halides, quaternary alk(en)ylpyridinium halides, and alk(en)ylmagnesium halides.

26. The method according to claim 25, wherein the alk(en)yl substitution contains from about 4 to about 18 carbons.

27. The method according to claim 25, wherein the cationic detergent is hexadecyltrimethylammonium bromide.

* * * * *